`US011364282B2`

(12) United States Patent
Unfer

(10) Patent No.: US 11,364,282 B2
(45) Date of Patent: Jun. 21, 2022

(54) COMPOSITIONS, USES AND METHODS FOR TREATMENT OF INFERTILITY AND SUBFERTILITY

(71) Applicant: LO.LI. PHARMA S.R.L., Rome (IT)

(72) Inventor: Vittorio Unfer, Rome (IT)

(73) Assignee: LO.LI. PHARMA S.R.L., Rome (IT)

( * ) Notice: Subject to any disclaimer, the term of this patent is extended or adjusted under 35 U.S.C. 154(b) by 0 days.

(21) Appl. No.: 16/647,715

(22) PCT Filed: Sep. 18, 2018

(86) PCT No.: PCT/EP2018/075203
§ 371 (c)(1),
(2) Date: Mar. 16, 2020

(87) PCT Pub. No.: WO2019/057709
PCT Pub. Date: Mar. 28, 2019

(65) Prior Publication Data
US 2020/0215165 A1 Jul. 9, 2020

(30) Foreign Application Priority Data
Sep. 19, 2017 (IT) .................... 102017000104446

(51) Int. Cl.
*A61K 38/38* (2006.01)
*A61K 31/7004* (2006.01)
*A61P 15/08* (2006.01)

(52) U.S. Cl.
CPC .......... *A61K 38/38* (2013.01); *A61K 31/7004* (2013.01); *A61P 15/08* (2018.01)

(58) Field of Classification Search
CPC ...... A61K 38/38; A61K 31/7004; A61P 15/08
See application file for complete search history.

(56) References Cited

U.S. PATENT DOCUMENTS

2014/0294795 A1* 10/2014 Hsia ................. A61K 33/18
424/94.1
2015/0237902 A1* 8/2015 Rosado Loria ...... A61K 31/122
514/5.6

FOREIGN PATENT DOCUMENTS

| CN | 104365997 A | 2/2015 | |
|---|---|---|---|
| WO | 2008155651 A2 | 12/2008 | |
| WO | 2013076121 A1 | 5/2013 | |
| WO | WO-2016020495 A1 * | 2/2016 | ........... A61K 31/592 |

OTHER PUBLICATIONS

Yang et al. (Year: 2016).*
International Search Report and Written Opinion for Corresponding International Application No. PCT/EP2018/075203 (11 Pages) (dated Dec. 12, 2018).
Costantino et al., "Metabolic and hormonal effects of myo-inositol in women with polycystic ovary syndrome: a double-blind trial",European Review for Medical and Pharmacological Sciences, 2009, vol. 13, No. 2, pp. 105-110.
Wang, T; et al., "Use of multi-angle laser light scattering and size-exclusion chromatography to characterize the molecular weight and types of aggregates present in commercial whey protein products." Journal of dairy science vol. 86,10 (2003): 3090-3101.

* cited by examiner

*Primary Examiner* — Jeffrey S Lundgren
*Assistant Examiner* — Ibrahim D Bori
(74) *Attorney, Agent, or Firm* — Lucas & Mercanti, LLP

(57) ABSTRACT

The present invention relates i.a. to compositions which are suitable for treatment of infertility or subfertility, in particular infertility or subfertility caused by polycystic ovary syndrome (PCOS)or anovulation, or which are suitable for treatment of PCOS or anovulation itself.

20 Claims, 1 Drawing Sheet
Specification includes a Sequence Listing.

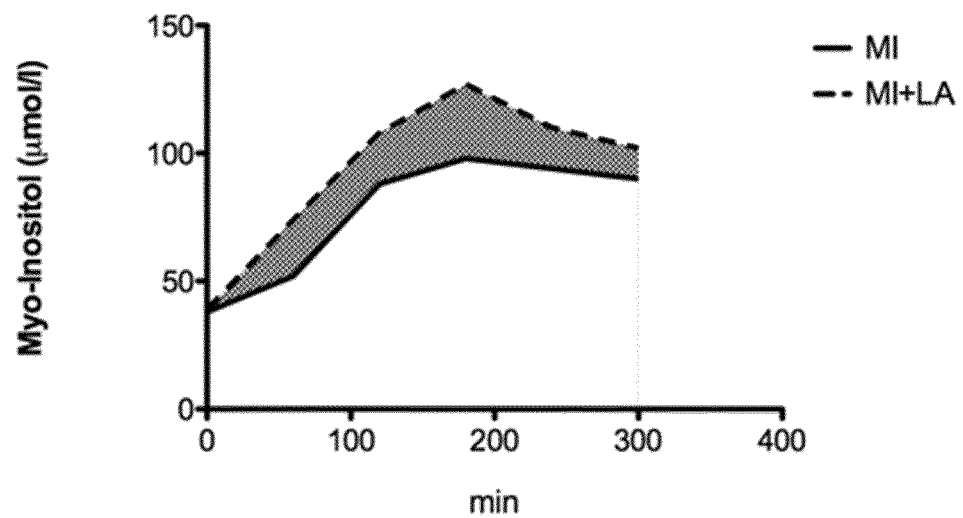

COMPOSITIONS, USES AND METHODS FOR TREATMENT OF INFERTILITY AND SUBFERTILITY

CROSS-REFERENCE TO RELATED APPLICATIONS

This application is a 371 of PCT/EP2018/075203, filed Sep.18, 2018, which claims the benefit of Italian Patent Application No. 102017000104446, filed Sep. 19, 2017.

The present invention relates to compositions which are suitable for treatment of infertility or subfertility, in particular infertility or subfertility caused by polycystic ovary syndrome (PCOS) or anovulation, or which are suitable for treatment of PCOS or anovulation itself. The compositions comprise inositol and alpha lactalbumin in defined weight ratios. The invention further relates to a combination of inositol and alpha lactalbumin for use as a medicament. The invention further relates to inositol in combination with alpha lactalbumin for use in a method of treating infertility or subfertility, in particular infertility or subfertility caused by PCOS or anovulation, or for use in a method of treating PCOS or anovulation itself. The invention further relates to a method of treating infertility or subfertility, in particular infertility or subfertility caused by PCOS or anovulation, or treating PCOS or anovulation itself. The invention further relates to a kit of parts comprising inositol and alpha lactalbumin. The invention further relates to a food product or drink product comprising inositol and alpha lactalbumin.

BACKGROUND OF THE INVENTION

Polycystic ovary syndrome (PCOS) is one of the most common female endocrine disorders with a variety of metabolic and endocrine abnormalities and clinical symptoms. It is a chronic condition with implications for morbidities, both in short-term, such as subfertility and pregnancy-related complications, as well as long-term risks such as diabetes, cardiovascular diseases, poor quality of life and overall mortality. The diagnostic traits of polycystic ovary syndrome are hyperandrogenism, chronic oligoovulation or anovulation, and polycystic ovaries. Medical treatment of PCOS aims to restore fertility, treat hirsutism (abnormal growth of hair on a woman's face and body) or acne, and restore ovulation.

It is known that inositol, in particular myoinositol, is effective in restoring spontaneous ovarian activity and, consequently, fertility in most patients with PCOS. For instance, oral treatment with 2 g myoinositol twice a day has been clinically investigated in several trials and can be considered one of the standard treatments of PCOS.

Despite this, neither inositol, in particular myoinositol, nor other pharmacological treatments (e.g. metformine, clomiphene citrate, etc.) are always completely effective in treating PCOS or associated conditions such as anovulation, fertility and subfertility in all patients. This could be related to varying individual responses to the same treatment. Indeed, Kamenov et al. (Gynecol. Endocrinol. February 2015; 31(2):131-5), reported that treatment of anovulatory PCOS women with 4 g/day myoinositol still resulted in 38.3% of non-responders, that is patients who, after said treatment, did not ovulate. Thus, while the important role of myoinositol in human reproduction is known, and while myoinositol supplementation has been proposed as a reliable treatment in women affected by PCOS, there is still significant room for improvement in the treatment of infertility or subfertility, in particular infertility or subfertility caused by PCOS or anovulation, with inositols, in particular with myoinositol.

Lactalbumin belongs to the broader class of "whey proteins", and is the albumin contained in milk and obtained from whey. It is present in the milk of many mammals, including human breastmilk. Lactalbumin exists in two distinct, yet structurally related forms, alpha lactalbumin and beta lactalbumin. Studies suggest that alpha lactalbumin exerts a gastroprotective activity in experimental gastric ulcer models induced by ethanol or stress (Matsumoto H, Shimokawa Y, Ushida Y, Toida T, Hayasawa H. New biological function of bovine alpha lactalbumin: protective effect against ethanol- and stress-induced gastric mucosal injury in rats. Biosci. Biotechnol. Biochem. May 2001; 65(5):1104-11). Alpha lactalbumin fortifies the mucus gel layer in gastric mucosa in vivo, increasing the mucin content of the mucus gel layer in rat gastric mucosa (Ushida Y, Shimokawa Y, Toida T, Matsui H, Takase M. Bovine alpha lactalbumin stimulates mucus metabolism in gastric mucosa. J. Dairy Sci. February 2007; 90(2):541-6). By glucagon-like peptide 2 (GLP-2) stimulation, alpha lactalbumin contributes to growth and maturation of the small intestine. For instance, it stimulates it the proliferation of, and suppresses apoptosis in, intestinal epithelial cells, resulting in increased crypt-villus height and small bowel mass. Alpha lactalbumin can serve as an illustrative example of a "hybrid moonlighting protein", the various functions of which depend on its location and environment, and range from participation in lactose biosynthesis in the lactating mammary gland, to contribution to the antiviral, antimicrobial, and antitumor activity of milk, and also include involvement in diverse transport functions. Furthermore, structure, conformational properties and functions of alpha lactalbumin are regulated by binding of metal ions. EP 1 228 707 A1 describes alpha lactalbumin as a prebiotic agent, as well as its use for the treatment of gastroenteritis and salmonella infection.

It is an aim of the present invention to provide improved compositions, uses and methods for alleviating medical conditions such as infertility and subfertility, in particular infertility and subfertility caused by PCOS or anovulation. It is also an aim of the present invention to provide improved compositions, uses and methods for alleviating such conditions as PCOS and anovulation themselves.

SUMMARY OF THE INVENTION

One aspect of the invention provides a composition comprising inositol and alpha lactalbumin, wherein inositol and alpha lactalbumin are present in a respective weight ratio of about 1:1-50:1.

A further aspect of the invention provides a combination of inositol and alpha lactalbumin for use as a medicament.

A further aspect of the invention provides inositol, for use in a method of treating or preventing infertility or subfertility, in particular infertility or subfertility caused by polycystic ovary syndrome (PCOS) or anovulation, in a subject, wherein the method comprises administering the inositol to the subject in combination with alpha lactalbumin. In a related aspect, the invention provides inositol, for use in a method of treating or preventing polycystic ovary syndrome (PCOS) or anovulation in a subject, wherein the method comprises administering the inositol to the subject in combination with alpha lactalbumin.

A further aspect of the invention provides a method of treating or preventing infertility or subfertility, in particular infertility of subfertility caused by polycystic ovary syndrome (PCOS) or anovulation, in a subject in need or potential need thereof, wherein the method comprises administering a therapeutically or prophylactically effective amount of inositol to the subject in combination with alpha lactalbumin. In a related aspect, the invention provides a method of treating or preventing polycystic ovary syndrome (PCOS) or anovulation in a subject in need or potential need thereof, wherein the method comprises administering a therapeutically or prophylactically effective amount of inositol to the subject in combination with alpha lactalbumin.

A further aspect of the invention provides a kit of parts comprising inositol in a first container, and alpha lactalbumin in a second container.

A further aspect of the invention provides a food product or drink product comprising inositol and alpha lactalbumin, in which the respective weight ratio of inositol to alpha lactalbumin is about 1:1-50:1.

BRIEF DESCRIPTION OF THE FIGURES

FIG. 1 is a plot of data obtained in a 2-phase study demonstrating that the plasma concentration of myoinositol was significantly higher in patients receiving myoinositol with alpha lactalbumin than in patients receiving myoinositol without alpha lactalbumin. The lower graph shows the plasma level of myoinositol versus time when myoinositol is administered alone. The upper graph shows the plasma level of myoinositol versus time when myoinositol is administered in combination with alpha lactalbumin. The shaded portion between the upper and lower graphs illustrates the increased area under the curve for myoinositol plasma concentration versus time achieved by combined administration of myoinositol and alpha lactalbumin, relative to administration of myoinositol alone.

DETAILED DESCRIPTION OF THE INVENTION

The following provides definitions of various terms and expressions used in the present application to describe the invention. Some terms (e.g. inositol, alpha lactalbumin, composition, etc.) are recited identically in the description of different aspects or embodiments of the invention. It is to be understood that definitions of terms and expressions used in more than one aspect of the invention apply equally to any aspect of the invention described herein in which those terms and expressions appear. This applies equally regardless of where, i.e. which section, within the present application such terms are defined or discussed.

In this application, the use of the singular (e.g. "a" or "the") may include the plural unless specifically stated otherwise. Further, the use of the term "including" as well as other grammatical forms such as "includes" and "included", is not limiting.

As used herein the term "comprising" has the broad standard meaning "including", "encompassing", or "containing". It includes the explicitly recited element(s), and also allows, but does not require, the presence of other or another element(s) not recited. In addition to this broad meaning, as used herein, the term "comprising" also encompasses the limiting meaning "consisting of", according to which only the explicitly recited element(s), and no other(s) are present. In addition, the term "comprising" also includes the meaning of "consisting essentially of", which means that other element(s) may be present beyond those explicitly recited, provided the additionally present element(s) does not alter the technical effect achieved by the explicitly recited element(s).

As used herein the term "about" when referring to a particular value, e.g. an endpoint or endpoints of a range, encompasses and discloses, in addition to the specifically recited value itself, a certain variation around the specifically recited value. Such a variation may for example arise from normal measurement variability, e.g. in the weighing or apportioning of various substances by methods known to the skilled person. The term "about" shall be understood as encompassing and disclosing a range of variability above and below an indicated specific value, said percentage values being relative to the specific recited value itself, as follows. The term "about" may encompass and disclose variability of ±5.0%. The term "about" may encompass and disclose variability of ±4.9%. The term "about" may encompass and disclose variability of ±4.8%. The term "about" may encompass and disclose variability of ±4.7%. The term "about" may encompass and disclose variability of ±4.6%. The term "about" may encompass and disclose variability of ±4.5%. The term "about" may encompass and disclose variability of ±4.4%. The term "about" may encompass and disclose variability of ±4.3%. The term "about" may encompass and disclose variability of ±4.2%. The term "about" may encompass and disclose variability of ±4.1%. The term "about" may encompass and disclose variability of ±4.0%. The term "about" may encompass and disclose variability of ±3.9%. The term "about" may encompass and disclose variability of ±3.8%. The term "about" may encompass and disclose variability of ±3.7%. The term "about" may encompass and disclose variability of ±3.6%. The term "about" may encompass and disclose variability of ±3.5%. The term "about" may encompass and disclose variability of ±3.4%. The term "about" may encompass and disclose variability of ±3.3%. The term "about" may encompass and disclose variability of ±3.2%. The term "about" may encompass and disclose variability of ±3.1%. The term "about" may encompass and disclose variability of ±3.0%. The term "about" may encompass and disclose variability of ±2.9%. The term "about" may encompass and disclose variability of ±2.8%. The term "about" may encompass and disclose variability of ±2.7%. The term "about" may encompass and disclose variability of ±2.6%. The term "about" may encompass and disclose variability of ±2.5%. The term "about" may encompass and disclose variability of ±2.4%. The term "about" may encompass and disclose variability of ±2.3%. The term "about" may encompass and disclose variability of ±2.2%. The term "about" may encompass and disclose variability of ±2.1%. The term "about" may encompass and disclose variability of ±2.0%. The term "about" may encompass and disclose variability of ±1.9%. The term "about" may encompass and disclose variability of ±1.8%. The term "about" may encompass and disclose variability of ±1.7%. The term "about" may encompass and disclose variability of ±1.6%. The term "about" may encompass and disclose variability of ±1.5%. The term "about" may encompass and disclose variability of ±1.4%. The term "about" may encompass and disclose variability of ±1.3%. The term "about" may encompass and disclose variability of ±1.2%. The term "about" may encompass and disclose variability of ±1.1%. The term "about" may encompass and disclose variability of ±1.0%. The term "about" may encompass and disclose variability of ±0.9%. The term "about" may encompass and disclose variability of ±0.8%. The term "about" may encompass and disclose variability of ±0.7%. The term "about" may encompass and disclose variability of ±0.6%. The term "about"

may encompass and disclose variability of ±0.5%. The term "about" may encompass and disclose variability of ±0.4%. The term "about" may encompass and disclose variability of ±0.3%. The term "about" may encompass and disclose variability of ±0.2%. The term "about" may encompass and disclose variability of 0.1%. The term "about", in reference to the particular recited value, may encompass and disclose that exact particular value itself, irrespective of any explicit mention that this exact particular value is included; even in the absence of an explicit indication that the term "about" includes the particular exact recited value, this exact particular value is still included in the range of variation created by the term "about", and is therefore disclosed. Unless stated otherwise, if the term "about" is recited before the first endpoint of a numerical range, this term refers to both the first endpoint of the range and the second endpoint of the range. For instance, a recited range of "about X to Y" should be read as "about X to about Y". The same applies for a recited range of weight ratios. For instance, a recited range of weight ratios of "about X:Y-A:B" should be read as a weight ratio of "(about X):(about Y)-(about A):(about B)".

Unless stated otherwise, the designation of a range in the present application using a hyphen ("-") separating two bracketing values X and Y, or two bracketing ratios, is to be understood as meaning and disclosing the specified range in which both endpoint values X and Y are included. The same applies to a range expressed as "from X to Y". Accordingly, the expressions of ranges as "X-Y", "of X to Y", "from X to Y", "of X-Y" and "from X-Y" are to be understood equivalently as meaning and disclosing a range encompassing the end value X, all values between X and Y, as well as the end value Y. In contrast, the designation of a range in the present application using the word "between" preceding two bracketing values X and Y, or two bracketing ratios, is to be understood as meaning and disclosing the specified range in which both endpoint values X and Y are excluded, but all values between the specified endpoint values X and Y are included.

As used herein, the term "composition" encompasses and discloses any physical entity comprising or consisting of or consisting essentially of the respective recited substances. The physical form of the composition is not restricted. For example, the term "composition" encompasses and discloses a powder in which the recited substances are each present in powder form. As a further example, the term "composition" also encompasses and discloses a liquid solution in which the recited substances are present in solubilized form. As a further example, the term "composition" also encompasses and discloses an emulsion in which the recited substances are present. As a further example, the term "composition" also encompasses and discloses a suspension in which the recited substances are present. In particular, the term "composition" may be a "pharmaceutical composition" as defined herein below, and may be formulated for a desired route of administration. As used and disclosed herein, the term "composition" also may be a composition suitable for oral delivery, e.g. in the form of a tablet, including but not limited to an effervescent tablet or a multilayer tablet, a powder, e.g. in the form of a sachet, a hard capsule, a soft gel capsule, a syrup, a cachet, a troche, ora lozenge, a pastille, e.g. a gummy pastille, a salve, ora liquid preparation. The term "composition" may also be a composition suitable for delivery by a non-oral route, for example in the form of a suppository, a tablet, a hard capsule, a soft gel capsule, a cream, a gel, a patch or a liquid. Further dosage forms of the composition as well as referred routes of administration are set out herein below.

As used herein, the term "inositol" encompasses and discloses the substance having chemical formula $C_6H_{12}O_6$ and a structure according to any of the 9 known isomers of inositol, that is:

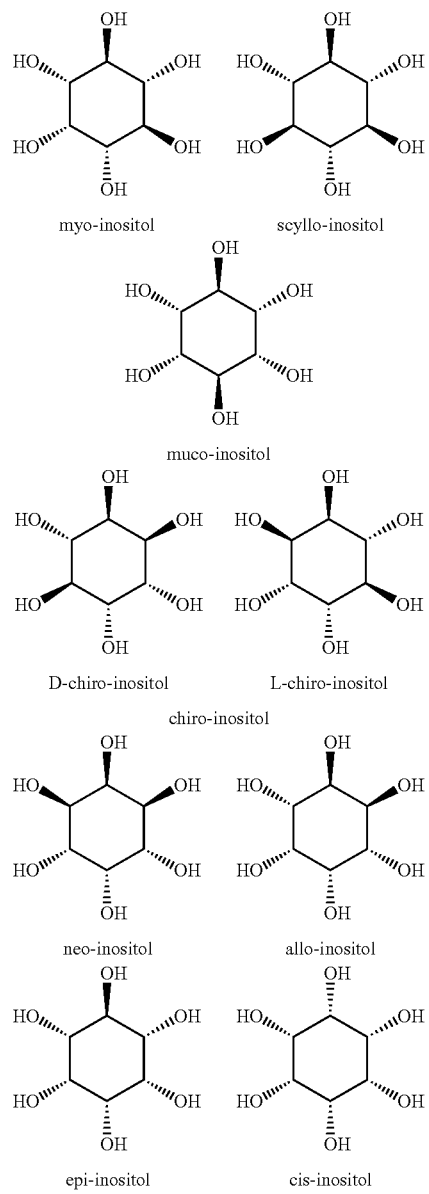

In a preferred embodiment of the present invention in any of the various aspects set out herein, the inositol is myoinositol. In another preferred embodiment of the present invention in any of the various aspects set out herein, the inositol is D-chiro-inositol. In another preferred embodiment of the present invention in any of the various aspects set out herein, the inositol is a mixture of myoinositol and D-chiro-inositol in any weight ratio. The weight ratio of myoinositol to D-chiro-inositol (myoinositol:D-chiro-inositol) in a mixture thereof may advantageously be from about 100:1 to 10:1, or may be between 100:1 and 10:1, or may be about 40:1. It is understood that in the case of a mixture of different types of inositol, the weight of "inositol", e.g. in the sense of any of the weight ratios mentioned herein, will be the sum of all types of inositol present.

As used herein, the term "alpha lactalbumin" means and discloses the known protein alpha lactalbumin present in the milk of mammalian species. As such, it can be readily isolated from the milk, in particular from the whey, of various mammalian milk, e.g. from cow milk, by established methods known to the skilled person, for example using chromatography/gel filtration, membrane separation, enzyme hydrolysis, and precipitation/aggregation technologies (Kamau S M, Cheison S C, Chen W, Liu X, Lu R. Alpha-Lactalbumin: Its Production Technologies and Bioactive Peptides. Comprehensive reviews in food science and food safety, 2010, 9, 197-212). Various orthologs of alpha lactalbumin are also commercially available for purchase, e.g. human alpha lactalbumin and bovine alpha lactalbumin. In particular, the "alpha lactalbumin" of the present invention may be human alpha lactalbumin (e.g. human alpha lactalbumin designated by CAS number 9013-90-5), bovine alpha lactalbumin (e.g. bovine alpha lactalbumin designated by CAS number 9051-29-0), ovine alpha lactalbumin, caprine alpha lactalbumin, donkey alpha lactalbumin, camel alpha lactalbumin, horse alpha lactalbumin, porcine alpha lactalbumin, buffalo alpha lactalbumin. Because of the wide availability, and therefore low cost, of cow milk as a source of alpha lactalbumin, bovine alpha lactalbumin is particularly preferred. Also preferred is human alpha lactalbumin, either in a form isolated from human milk, or in recombinant form. Although human alpha lactalbumin or recombinant human alpha lactalbumin can be employed by any route of administration herein, human alpha lactalbumin or recombinant human alpha lactalbumin is especially preferred if the route of administration of the inventive compositions or in the inventive uses and methods is intended to be parenteral, e.g. by infusion.

Human alpha lactalbumin precursor has 142 amino acids in the following sequence (NCBI accession number NP_002280; https://www.ncbi.nlm.nih.gov/protein/NP_002280):

(SEQ ID NO: 1)
MRFFVPLFLVGILFPAILAKQFTKCELSQLLKDIDGYGGIALPELICTMFH
TSGYDTQAIVENNESTEYGLFQISNKLWCKSSQVPQSRNICDISCDKFLDD
DITDDIMCAKKILDIKGIDYWLAHKALCTEKLEQWLCEKL.

The 19 amino acid signal peptide at the N-terminus of SEQ ID NO: 1 is underlined in the above sequence. The mature form of human alpha lactalbumin corresponds to amino acids 20-142 (inclusive) of SEQ ID NO: 1, i.e. the portion of SEQ ID NO: 1 as shown above which is not underlined. For example, the following nucleic acid sequence (NCBI accession number NM_002289; https://www.ncbi.nlm.nih.gov/nuccore/NM_002289) encodes SEQ ID NO: 1 above, and may be used in the production of recombinant human alpha lactalbumin:

```
                                                    (SEQ ID NO: 2)
  1  atttcaggtt cttggggta gccaaaatga ggttctttgt ccctctgttc ctggtgggca 61  tcctgttccc tgccatcctg gccaagcaat tcacaaaatg tgagctgtcc cagctgctga 121  aagacataga tggttatgga ggcatcgctt tgcctgaatt gatctgtacc atgtttcaca 181  ccagtggtta tgacacacaa gccatagttg aaaacaatga aagcacggaa tatggactct 241  tccagatcag taataagctt tggtgcaaga gcagccaggt ccctcagtca aggaacatct 301  gtgacatctc ctgtgacaag ttcctggatg atgacattac tgatgacata atgtgtgcca 361  agaagatcct ggatattaaa ggaattgact actggttggc ccataaagcc ctctgcactg 421  agaagctgga acagtggctt tgtgagaagt tgtgagtgtc tgctgtcctt ggcaccoctg 481  cccactccac actcctggaa tacctcttcc ctaatgccac ctcagtttgt ttctttctgt 541  tcccccaaag cttatctgtc tctgagcctt gggccctgta gtgacatcac cgaattcttg 601  aagactattt tccagggatg cctgagtggt gcactgagct ctagaccctt actcagtgcc 661  ttcgatggca ctttcactac agcacagatt tcacctctgt cttgaataaa ggtcccactt 721  tgaagtcaaa aaaaaaaaaa aa
```

Bovine alpha lactalbumin precursor has 142 amino acids in the following sequence (NCBI accession number NP_776803; https://www.ncbi.nlm.nih.gov/protein/NP_776803):

(SEQ ID NO: 3)
MMSFVSLLLVGILFHATQAEQLTKCEVFRELKDLKGYGGVSLPEWVCTTFH
TSGYDTQAIVQNNDSTEYGLFQINNKIWCKDDQNPHSSNICNISCDKFLDD
DLTDDIMCVKKILDKVGINYWLAHKALCSEKLDQWLCEKL

The 19 amino acid signal peptide at the N-terminus of SEQ ID NO: 3 is underlined in the above sequence. The mature form of bovine alpha lactalbumin corresponds to amino acids 20-142 (inclusive) of SEQ ID NO: 3, i.e. the portion of SEQ ID NO: 3 as shown above which is not underlined. For example, the following nucleic acid sequence (NCBI accession number NM_174378; https://www.ncbi.nlm.nih.gov/nuccore/NM_174378) encodes SEQ ID NO: 3 above, and may be used in the production of recombinant bovine alpha lactalbumin:

(SEQ ID NO: 4)

```
  1  atttcagaat cttgggggagt aaccaaaatg atgtcctttg tctctctgct cctggtaggc
 61  atcctattcc atgccaccca ggctgaacag ttaacaaaat gtgaggtgtt ccgggagctg
121  aaagacttga agggctacgg aggtgtcagt ttgcctgaat gggtctgtac cacgtttcat
181  accagtggtt atgacacaca agccatagta caaaacaatg acagcacaga atatggactc
241  ttccagataa ataataaaat ttggtgcaaa gacgaccaga accctcactc aagcaacatc
301  tgtaacatct cctgtgacaa gttcctggat gatgatctta ctgatgacat tatgtgtgtc
361  aagaagattc tggataaagt aggaattaac tactggttgg cccataaagc actctgttct
421  gagaagctgg atcagtggct ctgtgagaag ttgtgaacac ctgctgtctt tgctgcttct
481  gtcctctttc tgttcctgga actcctctgc cccgtggcta cctcgttttg cttctttgta
541  cccccttgaa gctaactcgt ctctgagccc tgggccctgt agtgacaatg gacatgtaag
601  gactaatctc caggggtgca tgaatggcgc tctggacttt tgaccttss tcgatgtccc
661  tgatggcgct tttaatgcaa cagtacatat tccacttttg tcccgaataa aaagcctgat
721  tttg
```

Ovine alpha lactalbumin precursor has 142 amino acids in the following sequence (NCBI accession number NP_001009797; https://www.ncbi.nlm.nih.gov/protein/NP_001009797):

(SEQ ID NO: 5)

MMSFVSLLLVGILFHATQAEQLTKCEAFQKLKDLKDYGGVSLPEWVCTAFH
TSGYDTQAIVQNNDSTEYGLFQINNKIWCKDDQNPHSRNICNISCDKFLDD
DLTDDIVCAKKILDKVGINYWLAHKALCSEKLDQWLCEKL

The 19 amino acid signal peptide at the N-terminus of SEQ ID NO: 5 is underlined in the above sequence. The mature form of bovine alpha lactalbumin corresponds to amino acids 20-142 (inclusive) of SEQ ID NO: 5, i.e. the portion of SEQ ID NO: 5 as shown above which is not underlined. For example, the following nucleic acid sequence (NCBI accession number NM_001009797; https://www.ncbi.nlm.nih.gov/nuccore/NM_001009797) encodes SEQ ID NO: 5 above, and may be used in the production of recombinant ovine alpha lactalbumin:

(SEQ ID NO: 6)

```
  1  ttccaggatc ttaggggta accaaaatga tgtcctttgt ctctctgctc ctggtaggca
 61  tcctattcca tgccacccag gctgaacaat taacaaaatg tgaggcgttc cagaagctga
121  aggacttgaa ggactacgga ggtgtcagtt tgcctgaatg ggtctgtacc gcatttcata
181  ccagtggtta tgacacacaa gccatagtac aaaacaatga cagcacagaa tatggactct
241  tccagataaa taataaaatt tggtgcaaag acgaccagaa ccctcactca aggaacatct
301  gtaacatctc ctgtgacaag ttcctggatg atgatcttac tgatgacatt gtgtgtgcca
361  agaagattct ggataaagta ggaattaact actggttggc ccataaagca ctctgttctg
421  agaagctgga tcagtggctc tgtgagaagt tgtgaacacc tgctgtcttt gctgcttctg
481  ccctcttcct gttcctggaa ctcctctgcc ccttggctac ctcgttttgc ttctttgtac
541  cccttgaag ctaacttgtc tctgagccct gggccctgta gtggcgatgg acatgtaagg
601  actaatctct agggatgcat gaatggtgct cgggacattt gaccttgct cggtgccct
661  gatagcactt ttaatgcaac agtgcatatt ccacttctgt cctgaataaa aggcctgatt
721  ctg
```

Porcine alpha lactalbumin precursor has 141 amino acids in the following sequence (NCBI accession number NP_999525; https://www.ncbi.nlm.nih.gov/protein/NP_999525):

(SEQ ID NO: 7)
MMSFVSLLVVGILFPAIQAKQFTKCELSQVLKDMDGYGDITLPEWICTIFH
ISGYDTKTIVHDNGSTEYGLFQINNKLWCRDNQIQSKNICGISCDKFLDDD
LTDDMMCAKKILDNEGIDYWLAHKALCSEKLDQWLCEKM

The 19 amino acid signal peptide at the N-terminus of SEQ ID NO: 7 is underlined in the above sequence. The mature form of porcine alpha lactalbumin corresponds to amino acids 20-141 (inclusive) of SEQ ID NO: 7, i.e. the portion of SEQ ID NO: 7 as shown above which is not underlined. For example, the following nucleic acid sequence (NCBI accession number NM_214360; https://www.ncbi.nlm.nih.gov/nuccore/NM_214360) encodes SEQ ID NO: 7 above, and may be used in the production of recombinant porcine alpha lactalbumin:

(SEQ ID NO: 8)
```
  1 aaaatgatgt cctttgtctc tctcctcgtg gtggggattc tctttcctgc catccaggcc
 61 aagcaattta caaaatgtga gctgtcccag gtgctgaaag acatggatgg ctatggagac
121 atcactttgc ctgaatggat ctgtaccata tttcatatca gtggctatga cacaaaaacc
181 attgtgcatg acaatggcag cacagaatat ggactcttcc agatcaataa taaactctgg
241 tgcagagaca accagatcca gtcaaagaac atctgtggca tctcctgtga caaattcctg
301 gatgatgacc ttactgatga catgatgtgt gccaagaaga tcctggataa tgaagggatt
361 gactactggt tggcccataa agcactctgt tcagaaaaac tggatcagtg gctctgtgag
421 aagatgtgaa cacccgctgt cttgctgctt ctgccttctt tatgttcctg gaactcctct
481 tccctaaggc tacctcattt tacttctttg tatcctcttg aagctaattt gtctctctga
541 gccctgggcc ctgtagtgat tgttatccga acactattct ctagagatgc gtgactggtg
601 cactggatttt ttaacctttg ctcagtgccc ctgattggct gtactacaac agtggattca
661 ctgtctgaat aaagggctga tcttg
```

Caprine alpha lactalbumin precursor has 142 amino acids in the following sequence (NCBI accession number NP_001272564; https://www.ncbi.nlm.nih.gov/protein/NP_001272564):

(SEQ ID NO: 9)
MMSFVSLLLVGILFHATQAEQLTKCEVFQKLKDLKDYGGVSLPEWVCTAFH
TSGYDTQAIVQNNDSTEYGLFQINNKIWCKDDQNPHSRNICNISCDKFLDD
DLTDDIVCAKKILDKVGINYWLAHKALCSEKLDQWLCEKL

The 19 amino acid signal peptide at the N-terminus of SEQ ID NO: 9 is underlined in the above sequence. The mature form of caprine alpha lactalbumin corresponds to amino acids 20-142 (inclusive) of SEQ ID NO: 9, i.e. the portion of SEQ ID NO: 9 as shown above which is not underlined. For example, the following nucleic acid sequence (NCBI accession number NM_001285635; https://www.ncbi.nlm.nih.gov/nuccore/NM_001285635) encodes SEQ ID NO: 9 above, and may be used in the production of recombinant caprine alpha lactalbumin:

(SEQ ID NO: 10)
```
  1 gggggggtaac caaaatgatg tcctttgtct ctctgctcct ggtaggcatc ctgttccacg
 61 ccacccaggc tgaacaatta acaaaatgtg aggtgttcca gaagctgaag gacttgaagg
121 actacggagg tgtcagtttg cctgaatggg tctgtactgc atttcatacc agtggttatg
181 acacacaagc catagtacaa aacaatgaca gcacagaata tggactcttc cagataaata
241 ataaaatttg gtgcaaagac gaccagaacc ctcactcaag gaacatctgt aacatctcct
```

```
301  gtgacaagtt cctggatgat gatcttactg atgacattgt gtgtgccaag aagattctgg 361  ataaagtagg aattaactac tggttggccc ataaagcact ctgttctgag aagctggatc 421  agtggctctg tgagaagttg tgaacacctg ctgtctttgc tgcttctgtc ctctttctgt 481  tcctggaact cctctgcccc ttggctacct cgttttgctt ctttgtaccc ccttgaagct 541  aactcgtctc tgagccctgg gccctgtagt gacgatggac atgtaaggac taatctccag 601  ggatgcgtga atggtgctca ggacatttga cccttgctcg gtgcccctga tagcactttt 661  aatgcaacag tgcatattcc acttctgtcc tgaataaaag gcctgattct gaaaaaaaaa 721  aaaaaaaaaa aaaaa
```

Buffalo alpha lactalbumin precursor has 142 amino acids in the following sequence (NCBI accession number NP_001277865; https://www.ncbi.nlm.nih.gov/protein/NP_001277865):

(SEQ ID NO: 11)
MMSFVSLLLVGSLFHATQAEQLTKCEVFRELRDLKDYGGVSLPEWVCTAFH

TSGYDTQAIVQNNDSTEYGLFQINNKIWCKDDQNPHSSNICNISCDKFLDD

DLTDDIMCVKKILDKVGINYWLAHKALCSEKLDQWLCEKL

The 18 amino acid signal peptide at the N-terminus of SEQ ID NO: 11 is underlined in the above sequence. The mature form of buffalo alpha lactalbumin corresponds to amino acids 19-142 (inclusive) of SEQ ID NO: 11, i.e. the portion of SEQ ID NO: 11 as shown above which is not underlined. For example, the following nucleic acid sequence (NCBI accession number NM_001290936; https://www.ncbi.nlm.nih.gov/nuccore/NM_001290936) encodes SEQ ID NO: 11 above, and may be used in the production of recombinant buffalo alpha lactalbumin:

```
(SEQ ID NO: 12)
  1  atgatgtcct ttgtctctct gctcctggta ggcagcctat tccatgccac ccaggcagaa 61  caattaacaa aatgtgaggt gttccgggag ctgagagact tgaaggacta cggaggtgtc 121  agtttgcctg aatgggtctg taccgcgttt cataccagtg gttatgacac acaagccata 181  gtacaaaaca atgacagcac agaatatgga ctcttccaga taaataataa aatttggtgc 241  aaagacgacc agaaccctca ctcaagcaac atctgtaaca tctcctgtga caagttcctg 301  gatgatgatc ttactgatga cattatgtgt gtcaagaaga ttctggataa agtaggaatt 361  aactactggt tggcccataa agcactctgt tctgagaagc tggatcagtg gctctgtgag 421  aagttgtga
```

As used herein, the term a "source of folate" or grammatically related terms such as "folate source" means any compound which, when introduced into the body, provides a source of folate to the body. One such source of folate is folic acid having the art-accepted definition of the compound of chemical formula $C_{19}H_{19}N_7O_6$ designated N-(4-{[(2-amino-4-oxo-1,4-dihydropteridin-6-yl)methyl]amino}benzoyl)-L-glutamic acid (IUPAC designation (2S)-2-[[4-[(2-amino-4-oxo-1 H-pteridin-6-yl)methylamino]benzoyl]amino]pentanedioic acid), and having the chemical structure:

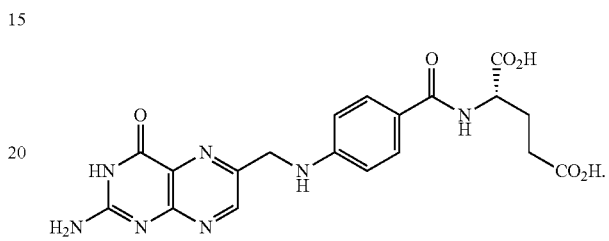

A source of folate may also be folate itself, e.g. in one of the salt forms of deprotonated folic acid. Another suitable source of folate is 5-methyltetrahydrofolate.

As used herein, the term "weight ratio" as applies to the relative amounts of two substances in e.g. composition, denotes the ratio of the weight of one compound relative to the weight of another compound in the respective composition. In particular, the weight ratio does not take account of the weight of any fillers, excipients, diluents, etc. which, in addition to the substances for which the weight ratio is specified, may also be present in the composition. As a particular nonbinding example, a composition comprising a weight ratio of inositol:alpha lactalbumin of 8:1 denotes a composition in which, by weight, the amount of inositol exceeds that of alpha lactalbumin by a factor of 8, regardless of the weight of any additional fillers, excipients, diluents, etc. which may be present in the composition. In the event the composition question is anything other than a solid composition, a specified weight ratio pertains to the weight amounts of components in that composition in their corresponding solid form, prior to solubilization, emulsification, suspension, etc. in the subject composition.

Although the present application mentions discrete embodiments, it is to be understood that any embodiment, and the features therein, may be freely combined with any other embodiment and the features therein, even in the absence of an explicit statement to this effect. Such combinations of one embodiment with another, or of one or more features in any one embodiment with one or more features in any other embodiment, thus belong to the disclosure of the present application as filed as understood by the skilled person.

Compositions Comprising Inositol and Alpha Lactalbumin

In addressing the problem of providing improved compositions, uses and methods for alleviating medical conditions such as infertility or subfertility, in particular infertility or subfertility caused by PCOS or anovulation, or for alleviating PCOS or anovulation itself, the inventors have surprisingly found that the advantageous effect due to administration of inositol, e.g. myoinositol alone or in mixture with D-chiro inositol, can be enhanced by combined administration with alpha lactalbumin. For instance, as described herein and shown in the later examples, the blood plasma levels of inositol, e.g. myoinositol, are higher following its combined administration with alpha lactalbumin, than following administration of inositol, e.g. myoinositol, without alpha lactalbumin. While not being bound by theory, the inventors believe that the increased plasma level of inositol, e.g. myoinositol, may be due to increased transfer through the wall of the gut in the presence of alpha lactalbumin. In view of this, the composition may preferably be a composition suitable for oral delivery, for example in the form of a tablet, including but not limited to an effervescent or multilayer tablet; a powder, e.g. a sachet; a hard capsule; a soft gel capsule; a syrup; a cachet; a troche; a lozenge; or a liquid preparation.

The surprising finding that combined administration of alpha lactalbumin with inositol entails important therapeutic advantages in the treatment and prevention of infertility and subfertility, especially infertility and subfertility caused by PCOS or anovulation, or the treatment and prevention of PCOS or anovulation itself. For instance, while many infertile, subfertile, anovulatory PCOS patients do respond well to treatment with myoinositol alone, a subset of these patients remains resistant to treatment with myoinositol alone. Importantly, the present inventors have found that combined administration of inositol, e.g. myoinositol, together with alpha lactalbumin can effectively treat those resistant patients who did not respond to inositol monotherapy. In this sense, the present invention allows recovery from infertility, subfertility, anovulation or PCOS in patients who, with existing therapies, would otherwise remain recalcitrant and untreatable. This has the ultimate effect of widening the scope of treating and preventing infertility, subfertility, anovulation and PCOS in women of childbearing age to an extent previously impossible.

Accordingly, one aspect of the present invention provides a composition comprising, consisting essentially of, or consisting of inositol and alpha lactalbumin, wherein inositol and alpha lactalbumin are present in the composition in a respective weight ratio of about 1:1-50:1. In one embodiment, inositol and alpha lactalbumin are present in the inventive composition in a respective weight ratio between 1:1 and 50:1. In another embodiment, inositol and alpha lactalbumin are present in the inventive composition in a respective weight ratio of about 8:1-50:1. In another embodiment, inositol and alpha lactalbumin are present in the inventive composition in a respective weight ratio between 8:1 and 50:1. In another embodiment, inositol and alpha lactalbumin are present in the inventive composition in a respective weight ratio of about 20:1-48:1. In another embodiment, inositol and alpha lactalbumin are present in the inventive composition in a respective weight ratio between 20:1 and 48:1. In another embodiment, inositol and alpha lactalbumin are present in the inventive composition in a respective weight ratio of about 25:1-46:1. In another embodiment, inositol and alpha lactalbumin are present in the inventive composition in a respective weight ratio between 25:1 and 46:1. In another embodiment, inositol and alpha lactalbumin are present in the inventive composition in a respective weight ratio of about 28:1-45:1. In another embodiment, inositol and alpha lactalbumin are present in the inventive composition in a respective weight ratio between 28:1 and 45:1. In another embodiment, inositol and alpha lactalbumin are present in the inventive composition in a respective weight ratio of about 30:1-44:1. In another embodiment, inositol and alpha lactalbumin are present in the inventive composition in a respective weight ratio between 30:1 and 44:1. In another embodiment, inositol and alpha lactalbumin are present in the inventive composition in a respective weight ratio of about 33:1-43:1. In another embodiment, inositol and alpha lactalbumin are present in the inventive composition in a respective weight ratio between 33:1 and 43:1. In another embodiment, inositol and alpha lactalbumin are present in the inventive composition in a respective weight ratio of about 35:1-42:1. In another embodiment, inositol and alpha lactalbumin are present in the inventive composition in a respective weight ratio between 35:1 and 42:1. In another embodiment, inositol and alpha lactalbumin are present in the inventive composition in a respective weight ratio of about 37:1-41:1. In another embodiment, inositol and alpha lactalbumin are present in the inventive composition in a respective weight ratio between 37:1 and 41:1. In another embodiment, inositol and alpha lactalbumin are present in the inventive composition in a respective weight ratio of about 39:1-41:1. In another embodiment, inositol and alpha lactalbumin are present in the inventive composition in a respective weight ratio between 39:1 and 41:1. In another especially preferred embodiment, inositol and alpha lactalbumin are present in the inventive composition in a respective weight ratio of about 40:1. In another especially preferred embodiment, inositol and alpha lactalbumin are present in the inventive composition in a respective weight ratio of 40:1. It is to be understood that each of the above weight ratios and weight ratio ranges pertains to the amounts of inositol and alpha lactalbumin which the inventive composition may comprise, consist essentially of, or consist of.

The skilled person will understand that the "composition" is intended to be used to treat or prevent certain pathological states as defined herein. The composition may also be used to address physiological states in which an increased intake of inositol is desireable. Accordingly, the composition of the invention may therefore be in a corresponding medicinal form, i.e. a pharmaceutical composition. In standing with compositions provided for the treatment or prevention of pathological states in the prior art, the skilled person will therefore understand that the inventive composition itself is not a food or a drink, i.e. is not itself a product which one would otherwise consume for sustenance. In particular, the inventive composition itself will not be a food product or a drink product (e.g. will not be a dairy product, e.g. a bovine milk-based product such as a whey-based product, or will not be a food bar, e.g. a grain-containing food bar), although such food products and drink products are described and covered as separate aspects of the present invention distinct from the inventive composition per se.

Various types of inositol and alpha lactalbumin have been set out above. Especially preferred is a combination of myoinositol and alpha lactalbumin in any of the above weight ratios. Also preferred is a combination of D-chiro-inositol and alpha lactalbumin in any of the above weight ratios. Also preferred is a mixture of myoinositol, D-chiro-inositol and alpha lactalbumin, wherein the inositol weight pertains to the combined weight of myoinositol and D-chiro-inositol. In such compositions comprising both myoinositol and D-chiro-inositol as the "inositol", the respective weight ratio of myoinositol and D-chiro-inositol (myoinositol:D-chiro-inositol) may be from about 10:1 to 100:1. The respective weight ratio of myoinositol and D-chiro-inositol may also be between 10:1 to 100:1. The respective weight ratio of myoinositol and D-chiro-inositol may also be from about 20:1 to 80:1. The respective weight ratio of myoinositol and D-chiro-inositol may also be between 20:1 and 80:1. The respective weight ratio of myoinositol and D-chiro-inositol may also be from about 30:1 to 60:1. The respective weight ratio of myoinositol and D-chiro-inositol may also be between 30:1 and 60:1. The respective weight ratio of myoinositol and D-chiro-inositol may also be from about 35:1 to 50:1. The respective weight ratio of myoinositol and D-chiro-inositol may also be between 35:1 and 50:1. The respective weight ratio of myoinositol and D-chiro-inositol may also be about 40:1. The respective weight ratio of myoinositol and D-chiro-inositol may also be 40:1.

It is understood that establishing a certain amount of inositol in the inventive composition is sufficient to automatically establish a corresponding amount of alpha lactalbumin in the inventive composition, in accordance with the above weight ratios of inositol:alpha lactalbumin. Adhering to the inositol: alpha lactalbumin weight ratios set out above ensures that the composition of the invention can achieve an advantageous technical effect in treating or preventing infertility or subfertility, especially infertility or subfertility caused by PCOS or anovulation, or in treating or preventing PCOS or anovulation itself. Nevertheless, the inventors have found that provision of a certain minimum amount of inositol in the inventive composition can be advantageous in ensuring that the desired therapeutic or prophylactic effect can be achieved in a reasonable number of administrations. Typically, successful treatment of infertility or subfertility, especially infertility or subfertility caused by PCOS or anovulation, as well as successful treatment of PCOS or anovulation itself, e.g. such that previously absent ovulation is reestablished, can be achieved by a daily administration of as much as about 6000 mg inositol, or about 4000 mg inositol. Of course, daily administration of this amount of inositol can be achieved using any composition adhering to the inositol: alpha lactalbumin weight ratios as described above, the only difference between compositions of different inositol: alpha lactalbumin weight ratios being the frequency with which such a composition must be administered in order to reach a given daily target amount of inositol. However, from the standpoint of the impact of any such repeated administration on patient quality of life, it can be advantageous to ensure a minimum amount of inositol in the composition so as to correspondingly decrease the number of daily administrations needed to reach a given daily target amount of inositol, e.g. the daily target amount of inositol indicated above.

Therefore, in certain embodiments, the composition of the invention may advantageously comprise as much as about 6000 mg inositol, or about 500-4000 mg of inositol. The composition of the invention may also advantageously comprise between 500 and 4000 mg of inositol. The composition of the invention may also preferably comprise about 1000-3000 mg of inositol. The composition of the invention may also preferably comprise between 1000 and 3000 mg of inositol. In especially preferred embodiments, the composition of the invention comprises about 600 mg inositol or about 2000 mg inositol. In further especially preferred embodiments, the composition of the invention comprises 600 mg inositol or 2000 mg of inositol. Especially the latter embodiments in which the composition of the invention comprises about 2000 mg inositol, 2000 mg of inositol, about 3000 mg of inositol, or 3000 mg of inositol, are especially advantageous because such compositions would need to be administered only twice a day in order to reach the daily target amount of as much as about 6000 mg inositol, or of 4000 mg inositol. An inventive composition comprising about 2000 mg of inositol, in which the weight ratio of inositol: alpha lactalbumin is e.g. about 8:1-50:1, or between 8:1-50:1, implies a corresponding amount of alpha lactalbumin ranging from about 40-250 mg, or between 40-250 mg, respectively. As mentioned above, a particularly advantageous inositol: alpha lactalbumin weight ratio is about 40:1 which, assuming about 2000 mg of inositol, e.g. myoinositol, in the inventive composition, implies about 50 mg of alpha lactalbumin in the inventive composition. Thus, inventive compositions comprising about 2000 mg of inositol and about 50 mg of alpha lactalbumin are especially preferred as striking an ideal balance between therapeutic efficacy and acceptable impact on patient quality of life.

Conversely, it is understood that establishing a certain amount of alpha lactalbumin in the inventive composition is sufficient to automatically establish a corresponding amount of inositol in the inventive composition, in accordance with the above weight ratios of inositol:alpha lactalbumin. In one embodiment, the inventive composition comprises about 10-500 mg alpha lactalbumin. In another embodiment, the inventive composition comprises between 10 and 500 mg alpha lactalbumin. In another embodiment, the inventive composition comprises about 20-100 mg alpha lactalbumin. In another embodiment, the inventive composition comprises between 20 and 100 mg alpha lactalbumin. In another embodiment, the inventive composition comprises about 30-70 mg alpha lactalbumin. In another embodiment, the inventive composition comprises between 30 and 70 mg alpha lactalbumin. In another embodiment, the inventive composition comprises about 50 mg alpha lactalbumin. In another embodiment, the inventive composition comprises 50 mg alpha lactalbumin. Assuming an inositol:alpha lactalbumin ratio of about 40:1, a composition comprising about 50 mg alpha lactalbumin implies about 2000 mg of inositol, e.g. myoinositol, in the same composition. Inventive compositions comprising about 2000 mg of inositol, e.g. myoinositol, and about 50 mg of alpha lactalbumin are thus especially preferred for the reasons set out above.

As set out herein above, the inositol in the inventive composition may be any one or more of the 9 isomers of inositol, in particular myoinositol, D-chiro-inositol, or a mixture thereof in any weight ratio of either, in particular those set out herein above. Preferably, the alpha lactalbumin is human or bovine alpha lactalbumin. In an especially preferred embodiment, the inventive composition comprises myoinositol and human alpha lactalbumin in a respective weight ratio of 40:1, for instance about 2000 mg myoinositol and about 50 mg human alpha lactalbumin.

In a further especially preferred embodiment, the inventive composition comprises myoinositol and bovine alpha lactalbumin in a respective weight ratio of 40:1, for instance about 2000 mg myoinositol and about 50 mg bovine alpha lactalbumin.

Compositions of the invention may further comprise a source of folate, preferably folic acid, i.e. N-(4-{[(2-amino-4-oxo-1,4-dihydropteridin-6-yl)methyl]amino}benzoyl)-L-glutamic acid. Adding a source of folate, preferably folic acid, to the inventive composition can be advantageous in view of folate's known importance in the gestation process, in particular in preventing deformations such as spina bifida. Considering the inventive composition's beneficial effect in treating or preventing infertility or subfertility, in particular infertility or subfertility caused by PCOS or anovulation, as well as in treating or preventing PCOS or anovulation itself, the inventive composition is likely to be taken by women of childbearing age who have tried unsuccessfully to become pregnant, in order to promote a desired pregnancy. In this event, having an accumulated store of folate is advantageous for proper gestation in the expected ensuing pregnancy. In the broadest sense, then, including a source of folate, preferably folic acid, in the inventive composition supports the downstream process which the inventive composition ultimately promotes. However, the source of folate, preferably folic acid, is not itself necessary for preventing or treating infertility or subfertility, in particular infertility or subfertility caused by PCOS or anovulation, nor is it necessary for preventing or treating PCOS or anovulation itself. Indeed, several controlled clinical trials relating to the treatment of PCOS have been carried out using folic acid as placebo and determined that no specific effect attributable to folic acid was found in the selected population (see e.g. Costantino D, Minozzi G, Minozzi E, Guaraldi C. Metabolic and hormonal effects of myo-inositol in women with polycystic ovary syndrome: a double-blind trial. Eur Rev Med Pharmacol Sci 2009; 13:105-10; Genazzani A D, Lanzoni C, Ricchieri F, Jasonni V M. Myo-inositol administration positively affects hyperinsulinemia and hormonal parameters in overweight patients with polycystic ovary syndrome. Gynecol Endocrinol. 2008; 24:139-44; and Gerli S, Papaleo E, Ferrari A, Di Renzo GC. Randomized, double blind placebo-controlled trial: effects of myo-inositol on ovarian function and metabolic factors in women with PCOS. Eur Rev Med Pharmacol Sci 2007; 11:347-54). Accordingly, the technical effect described herein relating to the treatment of infertility or subfertility, in particular infertility or subfertility caused by PCOS or anovulation, as well as relating to the treatment of PCOS or anovulation itself, can be achieved with inositol and alpha lactalbumin in dual combination alone, without a folate source, e.g. folic acid.

In one embodiment, the inventive composition comprises a source of folate, preferably folic acid, in a respective alpha lactalbumin:folate source weight ratio of about 1:0.001-1:0.01. In another embodiment, the alpha lactalbumin:folate source weight ratio is between 1:0.001 and 1:0.01. In another embodiment, the alpha lactalbumin:folate source weight ratio is about 1:0.002-1:0.008. In another embodiment, the alpha lactalbumin: folate source weight ratio is between 1:0.002-1:0.008. In another embodiment, the alpha lactalbumin:folate source weight ratio is about 1:0.003-1:0.006. In another embodiment, the alpha lactalbumin: folate source weight ratio is between 1:0.003-1:0.006. In another embodiment, the alpha lactalbumin:folate source weight ratio is about 1:0.004.

In another embodiment, the alpha lactalbumin: folate source weight ratio is 1:0.004. It is understood that the specific type of inositol in the inventive composition may be any of the inositol isomers or mixtures thereof set out hereinabove. For instance, in a preferred embodiment of the invention the composition comprises about 2000 mg inositol, about 50 mg alpha lactalbumin and about 200 μg folic acid. In an especially preferred embodiment of the invention, the composition comprises about 2000 mg myoinositol, about 50 mg human alpha lactalbumin and about 200 μg folic acid. In a further especially preferred embodiment of the invention, the composition comprises 2000 mg myoinositol, 50 mg human alpha lactalbumin and 200 μg folic acid. In a further especially preferred embodiment of the invention, the composition comprises about 2000 mg myoinositol, about 50 mg bovine alpha lactalbumin and about 200 μg folic acid. In a further especially preferred embodiment of the invention, the composition comprises 2000 mg myoinositol, 50 mg bovine alpha lactalbumin and 200 μg folic acid.

As described above, the inventive composition itself is intended for ultimate use in the treatment or prevention of certain pathological conditions. The composition may also be used to address physiological states in which an increased intake of inositol is desireable. As such, it will generally be manufactured according to processes established for the manufacture of pharmaceutical products. Accordingly, in one embodiment, the inventive composition is a pharmaceutical composition. The compositions of the invention, including pharmaceutical compositions, may further comprise at least one pharmaceutically acceptable ingredient. While the inventive composition, including the pharmaceutical composition, may itself be administered to a subject, it will be understood that adding one or more pharmaceutically acceptable ingredients beyond inositol and alpha lactalbumin may be advantageous in rendering the composition more suitable for direct administration to a subject by a given predetermined route. Accordingly, the inventive composition, including a "pharmaceutical composition", may be formulated to comprise, in addition to inositol and alpha lactalbumin, a pharmaceutically acceptable ingredient which renders the composition more suitable or especially suitable for direct administration to a subject by a given route, without further workup. This suitability may pertain to a number of different administration routes, including oral, parenteral, transmucosal, transurethral, transrectal, vaginal or perivaginal, topical, transdermal or intravesical, as further set out in the following. Where present, such ingredients as well as their advantageous impact on the suitability of the inventive composition for different routes of administration, are set out below.

a) Formulation of the Inventive Composition for Suitability for Oral Administration A composition of the invention suitable for oral administration may be prepared, packaged, or sold in the form of a discrete solid dose unit including a sachet (e.g. a powder in a sachet), a tablet, a hard or soft capsule, a cachet, a troche, or a lozenge, each containing a predetermined amount of inositol and alpha lactalbumin in a ratio as specified herein. Other formulations suitable for oral administration include a powdered or granular formulation, an aqueous or oily suspension, an aqueous or oily solution, or an emulsion. As used herein, an "oily" liquid comprises a carbon-containing liquid molecule that exhibits a less polar character than water.

It is especially preferred that the discrete solid dose unit of the inventive composition is in the form of a powder, especially presented in the form of a sachet. As used herein, the term "sachet" refers to a sealed pouch containing the inventive composition. The pouch may be made of paper, wax paper, plasticized paper, or a combination of paper and foil. The material out of which the sachet is fashioned is preferably impervious to ambient moisture and other potential atmospheric contaminants so that, by sealing said sachet, the inventive composition in the form of a powder contained therein remains in a free flowing form until use.

A tablet comprising the inositol and alpha lactalbumin may, for example, be made by compressing or molding the inositol and alpha lactalbumin, optionally with one or more additional ingredients. Compressed tablets may be prepared by compressing, in a suitable device, inositol and alpha lactalbumin in a free flowing form such as a powder or granular preparation, optionally mixed with one or more of a binder, a lubricant, an excipient, a surface active agent, and a dispersing agent. Molded tablets may for example be made by molding, in a suitable device, a mixture of inositol and alpha lactalbumin, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the inositol and alpha lactalbumin. Following ingestion, the composition of the invention will advantageously be released prior to passing to the small intestine, where primary inositol resorption takes place. By way of example, a material such as glyceryl monostearate or glyceryl distearate may be used to coat tablets. Tablets may further comprise a sweetening agent, a flavoring agent, a coloring agent, a preservative, or some combination of these in order to provide pharmaceutically attractive and palatable preparation.

Hard capsules comprising the inositol and alpha lactalbumin may be made using a physiologically degradable composition, such as gelatin or cellulose derivatives. Such hard capsules comprise the inositol and alpha lactalbumin, and may further comprise additional ingredients including, for example, an inert solid diluent such as calcium carbonate, calcium phosphate, or kaolin.

Soft gelatin capsules comprising the inositol and alpha lactalbumin may be made using a physiologically degradable composition, such as gelatin combined with a plasticizer (i.e. glycerol) as basic component of the soft gelatin shell. Soft gelatin capsules may contain a liquid or semisolid solution, suspension, or microemulsion preconcentrate. The soft capsule filling comprises the inositol and alpha lactalbumin, which may be mixed with water or an oil medium such as peanut oil, liquid paraffin, olive oil, soybean oil, sunflower oil, a lecithin such as for example soy lecithin or sunflower lecithin, medium chain triglycerides, polyglycerol oleate, beeswax, mono- and diglycerides of fatty acids, or combinations of any of the above.

Liquid formulations of the composition of the invention that are especially suitable for oral administration may be prepared, packaged, and sold either in liquid form or in the form of a dry product intended for reconstitution with water or another suitable vehicle prior to ingestion.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropyl methylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Powdered and granular formulations of a composition, e.g. a pharmaceutical composition of the invention may be prepared using known methods. Such formulations may be administered directly to a subject, used, for example, to form sachet or tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

The composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (e.g. such as with a physiologically degradable material), and methods of absorbing an aqueous or oily solution or suspension into an absorbent material, with or without subsequent drying.

b) Formulation of the Inventive Composition for Suitability for Parenteral Administration For parenteral administration, the composition of the invention comprising inositol and alpha lactalbumin may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other agents such as suspending, stabilizing and/or dispersing agents such as those mentioned above, may be used.

When formulating the composition of the invention for parenteral administration to a subject, it can be advantageous to provide the alpha lactalbumin in the form of human alpha lactalbumin, e.g. recombinant human alpha lactalbumin as explained herein above. In this way, one can minimize the risk of triggering unwanted immunogenic reactions in the subject against non-human protein substances.

The composition of the invention comprising inositol and alpha lactalbumin may be rendered especially suitable for parenteral administration by formulation with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules, crushable or otherwise, or in multi-dose containers containing a preservative. Compositions especially suitable for parenteral administration include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of the inventive composition which is especially suitable for parenteral administration, the active ingredient is provided in dry (e.g. powder or granular) form for reconstitution with a suitable vehicle (e.g. sterile pyrogen free water) prior to parenteral administration of the reconstituted composition.

The inventive composition may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable compositions may be prepared using a non toxic, parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or diglycerides. Other usual parentally-administrable formulations include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

c) Formulation of the Inventive Composition for Suitability for Transmucosal Administration The inventive composition comprising inositol and alpha lactalbumin may be formulated to be suitable for transmucosal administration. The formulation may include any substances or dosage unit suitable for application to mucosal tissue. For example, the selected active agent may be administered to the buccal mucosa in an adhesive tablet or patch, sublingually administered by placing a solid dosage form under the tongue, lingually administered by placing a solid dosage form on the tongue, administered nasally as droplets or a nasal spray, a non-aerosol liquid formulation, or a dry powder, placed within or near the rectum ("transrectal" formulations), or administered to the urethra as a suppository, ointment, or the like.

d) Formulation of the Inventive Composition for Suitability for Transurethal Administration The inventive composition comprising inositol and alpha lactalbumin may also be formulated to be suitable for transurethal administration. In this case, the inventive composition may comprise a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials. A transurethral permeation enhancer may be included in the dosage from. Examples of suitable permeation enhancers include dimethylsulfoxide ("DMSO"), dimethyl formamide ("DMF"), N,N-dimethylacetamide ("DMA"), decylmethylsulfoxide ("C10 MSO"), polyethylene glycol monolaurate ("PEGML"), glycerol monolaurate, lecithin, the 1-substituted azacycloheptan-2-ones, particularly 1-n-dodecyl-cyclazacycloheptan-2-one, surfactants as discussed above, including, for example TWEEN-80™, and lower alkanols such as ethanol.

e) Formulation of the Inventive Composition for Suitability for Transrectal Administration The inventive composition comprising inositol and alpha lactalbumin may also be formulated to be suitable for transrectal administration. Transrectal dosage forms may include rectal suppositories, creams, ointments, and liquid formulations (enemas). The suppository, cream, ointment or liquid formulation for transrectal delivery comprises inositol and alpha lactalbumin and one or more conventional nontoxic carriers suitable for transrectal drug administration.

The transrectal dosage forms of the inventive composition may be manufactured using conventional processes. The transrectal dosage unit may be fabricated to disintegrate rapidly or over a period of several hours. The time period for complete disintegration may be in the range of from about 10 minutes to about 6 hours, e.g., less than about 3 hours.

f) Formulation of the Inventive Composition for Suitability for Vaginal or Perivaginal Administration The inventive composition comprising inositol and alpha lactalbumin may also be formulated to be especially suitable for vaginal or perivaginal administration. Suitable dosage forms to this end may include vaginal suppositories, creams, ointments, liquid formulations, pessaries, tampons, gels, pastes, foams or sprays. The suppository, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as for example disclosed in Remington: The Science and Practice of Pharmacy, supra. The vaginal or perivaginal dosage unit may be fabricated to disintegrate rapidly or over a period of several hours. The time period for complete disintegration may be in the range of from about 10 minutes to about 6 hours, e.g., less than about 3 hours.

g) Formulation of the Inventive Composition for Suitability for Topical Formulations The inventive composition comprising inositol and alpha lactalbumin may also be formulated to be especially suitable for topical administration. Suitable dosage forms to this end may include any form suitable for application to the body surface, and may comprise, for example, an ointment, cream, gel, lotion, solution, paste or the like, and/or may be prepared so as to contain liposomes, micelles, and/or microspheres. In certain embodiments, topical formulations herein are ointments, creams and gels.

h) Formulation of the Inventive Composition for Suitability for Transdermal Administration The inventive composition comprising inositol and alpha lactalbumin may also be formulated to be especially suitable for transdermal administration. As known to one skilled in the art, transdermal administration involves the delivery of pharmaceutical compounds via percutaneous passage of the compound into the systemic circulation of the patient. This can be affected e.g. by transdermal patches or iontophoresis devices. Other components besides inositol and alpha lactalbumin may be incorporated into the transdermal patches as well. For example, compositions and/or transdermal patches may be formulated with one or more preservatives or bacteriostatic agents including, but not limited to, methyl hydroxybenzoate, propyl hydroxybenzoate, chlorocresol, benzalkonium chloride, and the like. Dosage forms of the inventive composition for topical administration of the inositol and alpha lactalbumin may include creams, sprays, lotions, gels, ointments, eye drops, nose drops, ear drops, and the like. In such dosage forms, the ingredients of the inventive composition may be mixed to form a white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions may contain polyethylene glycol 400. They may be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, may be impregnated with the compositions in solution, lotion, cream, ointment or other such form may also be used for topical application. The compositions may also be applied topically using a transdermal system, such as one of an acrylic-based polymer adhesive with a resinous crosslinking agent impregnated with the composition and laminated to an impermeable backing.

Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir that, in this case, may be either a polymeric matrix as described above, or be a liquid or hydrogel reservoir, or take some other form.

i) Formulation of the Inventive Composition for Suitability for Intravesical Administration The term intravesical administration is used herein in its conventional sense to mean delivery of a drug directly into the bladder. Suitable methods for intravesical administration may be found, for example, in U.S. Pat. Nos. 6,207,180 and 6,039,967.

Therapeutic Uses and Methods

As described herein, the inventors have found that the therapeutic effect of inositol in treating or preventing infertility or subfertility, in particular infertility or subfertility caused by PCOS or anovulation, or in treating or preventing PCOS or anovulation and itself, is enhanced by coadministration of alpha lactalbumin. The inventors are aware of no therapeutic or prophylactic use of inositol and alpha lactalbumin together in the same regimen let alone for any of the purposes indicated above.

Accordingly, a further aspect of the invention provides a combination of inositol and alpha lactalbumin for use of a medicament. The inositol may be chosen from the types of inositol and inositol mixtures set out above. The alpha lactalbumin is as defined hereinabove. As explained above, combining inositol and alpha lactalbumin in the same regimen has the surprising effect of extending inositol's known therapeutic effect to individuals which otherwise would remain resistant to inositol therapy alone.

As used herein, the term "combination", or the expression "in combination with" with reference to inositol and alpha lactalbumin, refers to the coupling of inositol and alpha lactalbumin for the purpose of their coadministration to a subject within a given treatment regimen. A given treatment regimen will typically comprise multiple, repeated coadministrations of inositol and alpha lactalbumin over a predetermined time course, e.g. over 1 month, over 2 months, over 3 months, over 4 months or over 5 months or more, a time course of at least 3 months being preferred. The coadministration of inositol and alpha lactalbumin may be repeated multiple times daily, for example once, twice, 3 times, 4 times, 5 times or more, a repetition about twice daily being preferred. That is, the coadministration of inositol and alpha lactalbumin is repeated over a predetermined length of time, and the sum of the instances of coadministration over this predetermined length of time constitutes the prophylactic or therapeutic regimen.

The coupling of inositol and alpha lactalbumin meant by a "combination" of these two substances need not be physical, nor need it imply simultaneity of administration. Reference to a "combination" of inositol and alpha lactalbumin therefore encompasses and discloses multiple possibilities regarding the route and timing of administration of the respective substances. Encompassed and disclosed in the meaning of "combination" is for example the coupling of inositol and alpha lactalbumin for simultaneous administration by the same route, simultaneous administration by different routes, chronologically staggered administration by the same route, or chronologically staggered administration by different routes. Any of the administration routes described hereinabove may be combined in any way, although it will generally be preferable that the route will be oral. Especially preferable is simultaneous administration of inositol and alpha lactalbumin by the oral route, e.g. when inositol and alpha lactalbumin are present in a composition, e.g. in one of the inventive compositions set out herein, e.g. in the form of a tablet, hard capsule, soft gel capsule, or powder, e.g. in the form of a sachet, for ingestion.

Simultaneous administration of inositol and alpha lactalbumin by the same route might for example take the form of inositol and alpha lactalbumin being comprised in the same physical composition, that composition being administered to, e.g. ingested by, the subject so that the inositol and alpha lactalbumin enter the body by the same route, e.g. by the oral route, at the same time. Coupling of inositol and alpha lactalbumin for staggered administration within a given coadministration is however also possible, and is also encompassed and disclosed in the term "combination". The order of administration of alpha lactalbumin and inositol is not particularly important; the chronologically staggered administration of inositol and alpha lactalbumin might encompass prior administration of alpha lactalbumin and subsequent administration of inositol, or prior administration of inositol and subsequent administration of alpha lactalbumin. For example, staggered administration of inositol and alpha lactalbumin by the same route may take the form of initial oral administration of alpha lactalbumin, followed by oral administration of inositol; coupling of inositol and alpha lactalbumin in this way falls within the meaning of, and is disclosed by, "combination" as used herein. Conversely, staggered administration of inositol and alpha lactalbumin by different routes might take the form of initial oral administration of alpha lactalbumin, followed by administration of inositol by e.g. rectal or vaginal suppository; coupling of inositol and alpha lactalbumin in this way also falls within the meaning of, and is disclosed by, "combination" as used herein.

There are no particular restrictions on the duration of time between administration of inositol and alpha lactalbumin in the event the coadministration is chronologically staggered, however it will generally be most effective and convenient when any interim between administering inositol and alpha lactalbumin is brief, approaching simultaneity, e.g. on the order of minutes. In rare cases such an interim may extend up to about an hour or several hours between respective administrations. The inventors have observed that the prolonged intake of alpha lactalbumin improves the bioavailability of inositol, in particular myoinositol, even after as long as 12 hours. In rare cases, then, in the event that the coadministration of inositol and alpha lactalbumin is chronologically staggered, the interim between administration in some instances may be as long as 12 hours. However, even in the event the inositol and alpha lactalbumin are administered in a chronologically staggered manner, whether by the same or different routes, the term "combination" means that a given coadministration of both inositol and alpha lactalbumin within any regimen will have been completed, i.e. both substances will have been administered, by the time the respective next coadministration of inositol and alpha lactalbumin (which itself may again be either simultaneous or chronologically staggered by the same or different routes) within the same regimen ensues.

In certain embodiments, the combination of inositol and alpha lactalbumin entails a combination in a respective inositol: alpha lactalbumin weight ratio of about 1:1-50:1, or any of the other respective weight ratios or weight ratio ranges set out hereinabove for the inventive composition itself. It is to be understood that each of these weight ratios and weight ratio ranges pertains to the amounts of inositol and alpha lactalbumin which the combination may comprise, consist essentially of, or consist of.

In one embodiment, in the combination of inositol and alpha lactalbumin for use as a medicament, the inositol is chosen from myoinositol, D-chiro inositol or a mixture thereof in any weight ratio. In a further embodiment, in the combination of inositol and alpha lactalbumin for use as a medicament, the combination is in the form of a composition of the invention as described hereinabove, i.e. a composition comprising inositol and alpha lactalbumin, wherein inositol and alpha lactalbumin are present in a respective inositol: alpha lactalbumin weight ratio of about 1:1-50:1. In a further embodiment, in the combination of inositol and alpha lactalbumin for use as a medicament, the combination is in the form of a composition of the invention as described hereinabove in any one of its embodiments.

A further aspect of the invention provides inositol for use in a method of treating or preventing infertility or subfertility, in particular infertility or subfertility caused by polycystic ovary syndrome (PCOS) or anovulation, in a subject, wherein the method comprises administering the inositol to the subject in combination with alpha lactalbumin. In a related aspect, the invention provides inositol, for use in a method of treating or preventing polycystic ovary syndrome (PCOS) or anovulation in a subject, wherein the method comprises administering the inositol to the subject in combination with alpha lactalbumin. The term "combination" is to be understood in the sense explained hereinabove.

A further aspect of the invention provides inositol for use in a method of treating or preventing infertility or subfertility, in particular infertility having its origin in idiopathic infertility, in a subject, wherein the method comprises administering the inositol to the subject in combination with alpha lactalbumin. In a related aspect, the invention provides inositol for use in a method of treating or preventing idiopathic infertility in a subject, wherein the method comprises administering the inositol to the subject in combination with alpha lactalbumin. The term "combination" is to be understood in the sense explained hereinabove.

A further aspect of the invention provides a use of inositol in combination with alpha lactalbumin in the manufacture of a medicament for treating or preventing infertility or subfertility, in particular infertility or subfertility caused by polycystic ovary syndrome (PCOS) or anovulation. In a related aspect, the invention provides a use of inositol in combination with alpha lactalbumin in the manufacture of a medicament for treating or preventing polycystic ovary syndrome (PCOS) or anovulation. The term "combination" is to be understood in the sense explained hereinabove.

A further aspect of the invention provides a use of inositol in combination with alpha lactalbumin in the manufacture of a medicament for treating or preventing infertility or subfertility, in particular infertility having its origin in idiopathic infertility. In a related aspect, the invention provides a use of inositol in combination with alpha lactalbumin in the manufacture of a medicament for treating or preventing idiopathic infertility. The term "combination" is to be understood in the sense explained hereinabove A further aspect of the invention provides a method of treating or preventing infertility or subfertility, in particular a method of treating or preventing infertility of subfertility caused by polycystic ovary syndrome (PCOS) or anovulation, in a subject in need or potential need thereof, wherein the method comprises administering a therapeutically or prophylactically effective amount of inositol to the subject in combination with alpha lactalbumin. In a related aspect, the invention provides a method of treating or preventing polycystic ovary syndrome (PCOS) or anovulation in a subject in need or potential need thereof, wherein the method comprises administering a therapeutically or prophylactically effective amount of inositol to the subject in combination with alpha lactalbumin. The term "combination" is to be understood in the sense explained hereinabove.

A further aspect of the invention provides a method of treating or preventing infertility or subfertility, in particular a method of treating or preventing infertility having its origin in idiopathic infertility, in a subject in need or potential need thereof, wherein the method comprises administering a therapeutically or prophylactically effective amount of inositol to the subject in combination with alpha lactalbumin. In a related aspect, the invention provides a method of treating or preventing idiopathic infertility in a subject in need or potential need thereof, wherein the method comprises administering a therapeutically or prophylactically effective amount of inositol to the subject in combination with alpha lactalbumin. The term "combination" is to be understood in the sense explained hereinabove.

As used herein, the term "infertility", and grammatically related terms such as "infertile", describes a pathological state in which, despite repeated attempts over an extended time to become pregnant, no pregnancy has been achieved. Typically, a subject, that is a woman of childbearing age, who is "infertile" has not become pregnant despite repeated attempts to become pregnant, over a time period, e.g. about 1 year. A subject who is "infertile" will not normally become pregnant without medical, e.g. therapeutic intervention. Although infertility may have its origin in either of the genders, the infertility referred to herein is understood as female infertility, affecting a female subject of childbearing age.

As used herein, the term "subfertility", and grammatically related terms such as "subfertile", describes a pathological state in which attempts to become pregnant have a chance of succeeding, although such pregnancy will typically take longer to achieve than in normal subjects, i.e. about 6 months. "Subfertility" is thus the condition of being less than normally fertile, though still capable of achieving pregnancy. Typically, then, a subject, that is a woman of childbearing age, who is "subfertile" will typically need about 6 months of repeated attempts in order to become pregnant, but will still typically become pregnant within about 6 months to one year of trying. Although subfertility may have its origin in either of the genders, the subfertility referred to herein is understood as female subfertility, affecting a female subject of childbearing age.

As used herein, the term "idiopathic infertility", and grammatically related terms such as "idiopathically infertile", is considered to be a pathological state in which, despite repeated attempts over an extended time to become pregnant, no pregnancy has been achieved. Typically, a subject, that is a woman of childbearing age, who suffers from "idiopathic infertility" has not become pregnant despite repeated attempts to become pregnant, over a time period of, e.g. about 12 months (i.e. the inability to conceive after about 12 months of unprotected intercourse). A subject who is "idiopathically infertile" will not normally become pregnant without medical, e.g. therapeutic intervention. Although idiopathic infertility may have its origin in either of the genders, the idiopathic infertility referred to herein is understood as female idiopathic infertility, affecting a female subject of childbearing age. The term "idiopathic infertility", as used herein, is understood as being a subclass of infertility. For the purpose of this invention a woman experiencing an inability to become pregnant as above suffers from "idiopathic infertility" when, in addition to such observed inability to become pregnant, she tests negative for each of the following: hyperprolactinemia, hypothyroidism, Cushing's syndrome, adrenal hyperplasia, obesity, polycystic ovary syndrome (PCOS) and anovulation.

Of course, it is not always immediately apparent whether the cause for a failure to become pregnant is due to infertility or subfertility. From the vantage point of a woman of childbearing age trying to become pregnant, the only thing initially observed is that the desired pregnancy is not immediately achieved. A failure to become pregnant after one or 2 months may of course be due simply to chance, and after only that period of time the subject has no way of knowing whether the observed failure to become pregnant will persist for many more months. The classification of a woman of childbearing age as "subfertile" or "infertile" will therefore normally only be possible after a certain length of time of six months or twelve months respectively, when it becomes clear that the failure to achieve pregnancy is not due to mere chance, but may have other pathological causes. At that time, such suspected pathological causes may be further investigated.

As used herein, the term "anovulation" refers to a state in which the ovaries do not release an oocyte. Therefore, ovulation does not take place. Anovulation can be due to multiple factors such as PCOS, excessive stress, excessive exercise, a hormonal imbalance or any combination of these factors. The "anovulation" which is a cause of subfertility or infertility treated by the present invention, or which may itself be treated by the present invention, will not be anovulation due to genetic abnormalities, such as Turner's syndrome, physical deformities within the female reproductive system or normal physiological factors such as menopause.

As used herein, the term "oligoovulation" refers to a state in which ovulation is irregular or infrequent, but not completely absent.

As used herein, "polycystic ovary syndrome" (PCOS) denotes a condition in which 2 of the following 3 diagnostic traits are present: clinical or biochemical hyperandrogenism, chronic anovulation (or oligoovulation) and polycystic ovaries. These diagnostic criteria correspond to the consensus criteria established during the Rotterdam ESHRE-ASRM consensus workshop group in 2003. Although PCOS is diagnosed when 2 out of the above 3 criteria are fulfilled, treatment of PCOS in the sense of the present invention will abolish all 3 of the observable criteria mentioned above. Thus, treatment of PCOS in the sense of the present invention abolishes anovulation.

As used herein, the term "treat" or grammatically related variants thereof such as "treatment", "treating" etc. means the amelioration, even temporarily, encompassing but not requiring the complete abolishment of a pathological state. In the in the broadest sense, treatment of infertility or subfertility, by the medical uses and methods of treatment herein means achieving a pregnancy following a regimen of treatment as specified herein, where previous attempts to achieve pregnancy without applying such medical uses and methods of treatment have failed to result in the desired pregnancy. "Treatment" of PCOS means the at least temporary amelioration or abolishment of the three diagnostic criteria for PCOS as described herein. "Treatment" of anovulation means the at least temporary amelioration or abolishment of anovulation such that ovulation takes place at least once. "Treatment" of idiopathic infertility, means the at least temporary amelioration or abolishment of the diagnostic criteria of idiopathic infertility as defined herein, preferably such that biochemical pregnancy as determined by positive assay for human chorionic gonadotropin (beta hCG) is achieved, e.g. 14 days after ovulation.

As used herein, the term "prevent", and grammatically related terms such as "preventing", "prevention" etc. refer to scenarios in which the medical uses and methods of treatment described herein are applied to avert the possible, suspected or expected occurrence of infertility or subfertility, in particular of infertility or subfertility caused by PCOS or anovulation, or of PCOS or anovulation itself. Such suspicion that PCOS may be present may derive (even in the absence of a corresponding diagnosis) from the known frequency of PCOS as a cause for observed infertility or subfertility, e.g. in the case that infertility or subfertility has been determined, but in advance of a medical diagnosis of PCOS. Such suspicion or expectation that PCOS may be present may also derive from past experience, e.g. in the event that a subject was successful in becoming pregnant a first time, but experienced difficulties in doing so, and is attempting to become pregnant a second or further time. In such a case, the subject would have prior knowledge, from her previous pregnancy, that she is predisposed to infertility or subfertility, or even that she has or is predisposed to contract PCOS, and would therefore be justified in the expectation that similar difficulties would be experienced trying to become pregnant a second or further time. In this event, the subject matter of the invention could be applied in advance of, together with, or in advance of and together with attempts to become pregnant a further time so that such previously encountered difficulties are prevented. It will be understood that infertility or subfertility, especially infertility or subfertility caused by PCOS or anovulation, or PCOS or anovulation itself, may represent a subject's normal physiological state, which therapeutic intervention, e.g. with the subject matter of the present invention, need alleviate only temporarily to create a window of heightened fertility during which a desired pregnancy can be realized. After such desired pregnancy is achieved with the present invention, the subject may in the future revert, or may suspect reversion, to her normal physiological state of (e.g. PCOS-associated or anovulation-associated) infertility or subfertility, or of PCOS, suggesting that each subsequent attempt to become pregnant should be preceded by, accompanied by, or preceded and accompanied by the subject matter of the present invention. Such scenarios are within the meaning of "prevention" as used herein. Also within the definition of "prevention" as used herein is the administration of inositol and alpha lactalbumin to a subject before any diagnosis of infertility or subfertility, or before any diagnosis of PCOS or anovulation.

Equivalent considerations as outlined above apply for the "prevention" of infertility having its origin in idiopathic infertility, or for the prevention of idiopathic infertility itself.

As used herein, the phrase "caused by", e.g. as in "infertility or subfertility caused by PCOS or anovulation" denotes an at least partial causative relationship between PCOS or anovulation on the one hand and, on the other hand, infertility or subfertility. For example, PCOS may cause anovulation, which in turn causes infertility or subfertility. In this case, a causality would exist between PCOS and anovulation, as well as between both PCOS and anovulation on the one hand and, on the other hand, infertility or subfertility. In another example, a subject might be anovulatory, but not due to PCOS; this would for instance be the case when excessive stress or hormonal imbalances or excessive exercise bring about anovulation in the absence of PCOS. In such a scenario, a causality would exist between anovulation and infertility or subfertility. In yet another example, PCOS in a subject may be the direct cause of infertility or subfertility because of metabolic and hormonal anomalies attending PCOS, in the absence of anovulation, i.e. in cases were ovulation is normal despite a positive PCOS diagnosis (e.g. when a subject is positive for hyperandrogenism and polycystic ovaries but still ovulates). In this case, there would be a direct causality between PCOS and infertility or subfertility, and no causality between either PCOS and anovulation or anovulation and infertility or subfertility, anovulation being absent. In all of the above scenarios, the major sole or partial causes of infertility or subfertility, i.e. PCOS, anovulation or PCOS and anovulation, are treated or prevented. In doing so, infertility or subfertility, which is the ultimate consequence of PCOS and/or anovulation, is also simultaneously treated or prevented.

As used herein, the phrase "having its origin in", e.g. as in "infertility having its origin in idiopathic infertility" denotes an etiological relationship between idiopathic infertility on the one hand, and infertility on the other. This is the situation when a patient who is considered infertile has been diagnosed as "idiopathically infertile" according to the definition herein.

As used herein, the term "subject" means a female subject. As the compositions, uses and methods of the invention relate in the broadest sense to achieving pregnancy, it will be understood that the female subject is a premenopausal female subject of childbearing age. The terms "subject" and "patient" are used interchangeably herein.

The following embodiments apply equally to the above inositol for use in combination with alpha lactalbumin, the above uses of inositol in combination with alpha lactalbumin, and the above methods of treatment or prevention set out above.

In one embodiment, the inositol and the alpha lactalbumin are administered in combination to the subject non-simultaneously within a given combined administration of a given regimen. As used herein, the term "non-simultaneously" means that the inositol and the alpha lactalbumin are administered in a chronologically staggered manner, i.e. at different times. The administration refers to a respective coadministration of inositol and alpha lactalbumin within a broader regimen of treatment or prophylaxis. One embodiment entails administering the inositol to the subject prior to administering the alpha lactalbumin to the subject. Another embodiment entails administering the inositol to the subject following administering the alpha lactalbumin to the subject. It is understood that such non-simultaneous administration denotes any respective instance of coadministration of inositol and alpha lactalbumin within the broader context of the overall treatment regimen. As mentioned herein, regardless of the order of administration, that is inositol first and alpha lactalbumin second, or vice versa, the respective combined administration of inositol and alpha lactalbumin may be by the same or different routes.

In a further embodiment the inositol is administered to the subject simultaneously with alpha lactalbumin. As mentioned above, the simultaneous administration of inositol and alpha lactalbumin can be effected by the same or different routes. Most typically, it will be most advantageous and convenient to effect the simultaneous administration of inositol and alpha lactalbumin by the same route, preferably by an oral administration route. This will most often be accomplished by combining inositol and alpha lactalbumin in the same composition, for example in the form of a tablet, including but not limited to an effervescent tablet, a powder (especially presented in the form of a sachet), a hard capsule, a soft gel capsule, a syrup, a cachet, a troche, or a lozenge.

In further embodiments, the inositol and alpha lactalbumin are administered in combination in specific respective weight ratios of inositol to alpha lactalbumin (inositol:alpha lactalbumin). In one embodiment, inositol and alpha lactalbumin are administered in a respective weight ratio (inositol: alpha lactalbumin) of about 1:1-50:1. In one embodiment, inositol and alpha lactalbumin are administered in a respective weight ratio between 1:1 and 50:1. In another embodiment, inositol and alpha lactalbumin are administered in a respective weight ratio of about 8:1-50:1. In another embodiment, inositol and alpha lactalbumin are administered in a respective weight ratio between 8:1 and 50:1. In another embodiment, inositol and alpha lactalbumin are administered in a respective weight ratio of about 20:1-48:1. In another embodiment, inositol and alpha lactalbumin are administered in a respective weight ratio between 20:1 and 48:1. In another embodiment, inositol and alpha lactalbumin are administered in a respective weight ratio of about 25:1-46:1. In another embodiment, inositol and alpha lactalbumin are administered in a respective weight ratio between 25:1 and 46:1. In another embodiment, inositol and alpha lactalbumin are administered in a respective weight ratio of about 28:1-45:1. In another embodiment, inositol and alpha lactalbumin are administered in a respective weight ratio between 28:1 and 45:1. In another embodiment, inositol and alpha lactalbumin are administered in a respective weight ratio of about 30:1-44:1. In another embodiment, inositol and alpha lactalbumin are administered in a respective weight ratio between 30:1 and 44:1. In another embodiment, inositol and alpha lactalbumin are administered in a respective weight ratio of about 33:1-43:1. In another embodiment, inositol and alpha lactalbumin are administered in a respective weight ratio between 33:1 and 43:1. In another embodiment, inositol and alpha lactalbumin are administered in a respective weight ratio of about 35:1-42:1. In another embodiment, inositol and alpha lactalbumin are administered in a respective weight ratio between 35:1 and 42:1. In another embodiment, inositol and alpha lactalbumin are administered in a respective weight ratio of about 37:1-41:1. In another embodiment, inositol and alpha lactalbumin are administered in a respective weight ratio between 37:1 and 41:1. In another embodiment, inositol and alpha lactalbumin are administered in a respective weight ratio of about 39:1-41:1. In another embodiment, inositol and alpha lactalbumin are administered in a respective weight ratio between 39:1 and 41:1. In another especially preferred embodiment, inositol and alpha lactalbumin are administered in a respective weight ratio of about 40:1. In another especially preferred embodiment, inositol and alpha lactalbumin are administered in a respective weight ratio of 40:1. It is to be understood that each of these weight ratios and weight ratio ranges pertains to the amounts of inositol and alpha lactalbumin which the combination may comprise, consist essentially of, or consist of.

Various types of inositol and alpha lactalbumin have been set out above. Especially preferred in the medical uses and methods above is a combination of myoinositol and alpha lactalbumin in any of the above weight ratios. Also preferred is a combination of D-chiro-inositol and alpha lactalbumin in any of the above weight ratios. Also preferred is a mixture of myoinositol, D-chiro-inositol and alpha lactalbumin, wherein the inositol weight pertains to the combined weight of myoinositol and D-chiro-inositol. In such compositions comprising both myoinositol and D-chiro-inositol as the "inositol", the respective weight ratio of myoinositol and D-chiro-inositol (myoinositol:D-chiro-inositol) may be from about 10:1 to 100:1. The respective weight ratio of myoinositol and D-chiro-inositol may also be between 10:1 and 100:1. The respective weight ratio of myoinositol and D-chiro-inositol may also be from about 20:1 to 80:1. The respective weight ratio of myoinositol and D-chiro-inositol may also be between 20:1 and 80:1. The respective weight ratio of myoinositol and D-chiro-inositol may also be from about 30:1 to 60:1. The respective weight ratio of myoinositol and D-chiro-inositol may also be between 30:1 and 60:1. The respective weight ratio of myoinositol and D-chiro-inositol may also be from about 35:1 to 50:1. The respective weight ratio of myoinositol and D-chiro-inositol may also be between 35:1 and 50:1. Especially preferred, the respective weight ratio of myoinositol and D-chiro-inositol may also be about 40:1 or may be 40:1.

Adhering to the inositol:alpha lactalbumin weight ratios set out above ensures that the composition of the invention can achieve an advantageous technical effect in treating or preventing infertility or subfertility, especially infertility or subfertility caused by PCOS or anovulation, or in treating or preventing PCOS or anovulation itself. The inventors have found that provision of a certain minimum amount of inositol in the inventive composition can be advantageous in ensuring that the desired therapeutic or prophylactic effect can be achieved in a reasonable number of administrations. Typically, successful treatment or prevention of infertility or subfertility, especially infertility or subfertility caused by or associated with PCOS, as well as successful treatment or prevention of PCOS itself, e.g. such that previously absent ovulation is reestablished, can be achieved by a daily administration of a total of as much as about 6000 mg inositol, or about 4000 mg inositol. Of course, varying numbers of combined administrations of inositol and alpha lactalbumin may be necessary to achieve a given target daily administration of inositol, depending on how much inositol is administered in any one instance. However, from the standpoint of the impact of any such repeated administration on patient quality of life, it can be advantageous to ensure a minimum amount of inositol in the composition so as to correspondingly decrease the number of daily administrations needed to reach a given target amount of inositol, e.g. the target amount of inositol indicated above.

Therefore, certain embodiments of the above medical uses and treatment methods may advantageously comprise administering as much as about 6000 mg inositol, or about 500-4000 mg of inositol, or between 500 and 4000 mg of inositol, in any one combined administration. The above medical uses and treatment methods may also preferably comprise administering about 1000-3000 mg of inositol, or between 1000-3000 mg inositol in any one combined administration. The above medical uses and treatment methods may also preferably comprise administering about 2000 mg of inositol, 2000 mg of inositol, about 3000 mg of inositol, or 3000 mg of inositol, in any one combined administration. Especially the latter embodiments comprising administering about 2000 mg inositol, 2000 mg of inositol, about 3000 mg of inositol, or 3000 mg of inositol, are especially advantageous because such combined administration would be necessary only twice a day in order to reach a daily target amount of as much as about 6000 mg inositol, or about 4000 mg inositol. A combined administration entailing administration of about 2000 mg of inositol, in which the weight ratio of administered inositol:alpha lactalbumin is e.g. about 8:1-50:1, or between 8:1-50:1, implies a corresponding amount of administered alpha lactalbumin ranging from about 40-250 mg, or between 40-250 mg, respectively. As mentioned above, a particularly advantageous inositol:alpha lactalbumin weight ratio is about 40:1 which, assuming a combined administration entailing administration of about 2000 mg of inositol, implies administration of about 50 mg of alpha lactalbumin. Thus, combined administrations entailing administration of about 2000 mg of inositol, e.g. myoinositol, and about 50 mg of alpha lactalbumin are especially preferred as striking an ideal balance between therapeutic efficacy and acceptable impact on patient quality of life.

Conversely, it is understood that establishing a certain amount of alpha lactalbumin in the medical uses and methods of treatment above is sufficient to automatically establish a corresponding amount of inositol, in accordance with the above weight ratios of inositol:alpha lactalbumin. The above medical uses and treatment methods may also preferably comprise administering about 10-500 mg alpha lactalbumin, or between 10 and 500 mg alpha lactalbumin. The above medical uses and treatment methods may also preferably comprise administering about 20-100 mg alpha lactalbumin, or between 20 and 100 mg alpha lactalbumin. The above medical uses and treatment methods may also preferably comprise administering about 30-70 mg alpha lactalbumin, or between 30 and 70 mg alpha lactalbumin. The above medical uses and treatment methods may also preferably comprise administering about 50 mg alpha lactalbumin, or 50 mg alpha lactalbumin. Assuming an inositol:alpha lactalbumin ratio of about 40:1, administration of about 50 mg alpha lactalbumin implies administration of about 2000 mg of inositol in the same instance of combined administration. Medical uses and treatment methods as set out above which entail administering about 2000 mg of inositol, e.g. myoinositol, and about 50 mg of alpha lactalbumin are thus especially preferred for the reasons set out above.

As set out herein above, the inositol may be any one or more of the 9 isomers of inositol, in particular myoinositol, D-chiro-inositol, or a mixture thereof in any weight ratio of either, in particular those set out herein above. Preferably, the alpha lactalbumin is human alpha lactalbumin or bovine alpha lactalbumin. In an especially preferred embodiment, the medical uses and methods of treatment above comprise combined administration of myoinositol and human alpha lactalbumin in a respective weight ratio of 40:1, for instance about 2000 mg myoinositol and about 50 mg human alpha lactalbumin. In another especially preferred embodiment, the medical uses and methods of treatment above comprise combined administration of myoinositol and bovine alpha lactalbumin in a respective weight ratio of 40:1, for instance about 2000 mg myoinositol and about 50 mg bovine alpha lactalbumin.

A further embodiment of the above medical uses and methods of treatment further comprises administering a source of folate, preferably folic acid, to the subject in combination with inositol and alpha lactalbumin. Folic acid is understood as denoting the compound N-(4-{[(2-amino-4-oxo-1,4-dihydropteridin-6-yl)methyl]amino}benzoyl)-L-glutamic acid. The term "combination", as used in reference to folic acid, inositol and alpha lactalbumin, is to be understood analogously as explained above for the same term in reference to inositol and alpha lactalbumin only. Adding a source of folate, preferably folic acid, into the combination of substances administered can be advantageous in view of folic acid's known importance in the gestation process, in particular in preventing defects such as spina bifida. Considering the beneficial effect of the above medical uses and methods of treatment in treating or preventing infertility or subfertility, in particular infertility or subfertility caused by PCOS or anovulation, as well as in treating or preventing PCOS or anovulation itself, the subject in question will be a woman of childbearing age who has tried unsuccessfully to become pregnant, and who desires to promote a pregnancy. In this event, having an accumulated store of folate is advantageous for proper gestation in the expected ensuing pregnancy promoted by the medical uses and methods herein. In the broadest sense, then, combined administration of inositol, alpha lactalbumin and folic acid supports the downstream process which the inventive uses and method ultimately promote. However, the folate source, e.g. folic acid, is not itself necessary for preventing or treating infertility or subfertility, in particular infertility or subfertility caused by PCOS or anovulation, nor is it necessary for preventing or treating PCOS or anovulation itself. Indeed, several controlled clinical trials relating to the treatment of PCOS have been carried out using folic acid as placebo and determined that no specific effect attributable to folic acid was found in the selected population (see e.g. Costantino D, Minozzi G, Minozzi E, Guaraldi C. Metabolic and hormonal effects of myo-inositol in women with polycystic ovary syndrome: a double-blind trial. Eur Rev Med Pharmacol Sci 2009; 13:105-10; Genazzani A D, Lanzoni C, Ricchieri F, Jasonni V M. Myo-inositol administration positively affects hyperinsulinemia and hormonal parameters in overweight patients with polycystic ovary syndrome. Gynecol Endocrinol. 2008; 24:139-44; and Gerli S, Papaleo E, Ferrari A, Di Renzo GC. Randomized, double blind placebo-controlled trial: effects of myo-inositol on ovarian function and metabolic factors in women with PCOS. Eur Rev Med Pharmacol Sci 2007; 11:347-54). Accordingly, the technical effect described herein relating to the treatment of infertility or subfertility, in particular infertility or subfertility caused by PCOS or anovulation, as well as relating to the treatment of PCOS or anovulation itself, can be achieved with inositol and alpha lactalbumin in dual combination alone, without a folate source, e.g. folic acid.

In the event folic acid is administered in combination with inositol and alpha lactalbumin in the above medical uses and therapeutic methods, the weight amount of a folate source, preferably folic acid, in any one administration will generally be much less than the weight amount of either of the other two substances. For instance, in one embodiment of combined administration of folate source with inositol and alpha lactalbumin, the folate source may be administered in a respective alpha lactalbumin:folate source weight ratio of about 1:0.001-1:0.01. In another embodiment of combined administration of folate source with inositol and alpha lactalbumin, the folate source may be administered in a respective alpha lactalbumin:folate source weight ratio between 1:0.001 and 1:0.01. In another embodiment of combined administration of folate source with inositol and alpha lactalbumin, the folate source may be administered in a respective alpha lactalbumin:folate source weight ratio of about 1:0.002-1:0.008. In another embodiment of combined administration of folate source with inositol and alpha lactalbumin, the folate source may be administered in a respective alpha lactalbumin:folate source weight ratio between 1:0.002-1:0.008. In another embodiment of combined administration of folate source with inositol and alpha lactalbumin, the folate source may be administered in a respective alpha lactalbumin:folate source weight ratio of about 1:0.003-1:0.006. In another embodiment of combined administration of folate source with inositol and alpha lactalbumin, the folate source may be administered in a respective alpha lactalbumin:folate source weight ratio between 1:0.003-1:0.006. In another embodiment of combined administration of folate source with inositol and alpha lactalbumin, the folate source may be administered in a respective alpha lactalbumin:folate source weight ratio of about 1:0.004. In another embodiment of combined administration of folate source with inositol and alpha lactalbumin, the folate source may be administered in a respective alpha lactalbumin:folate source weight ratio of 1:0.004.

For instance, in one embodiment combined administration of inositol, alpha lactalbumin and a source of folate, preferably folic acid, comprises combined administration of about 2000 mg inositol, about 50 mg alpha lactalbumin and about 200 µg folic acid. It is understood that the specific type of inositol administered may be any of the inositol isomers or mixtures thereof set out hereinabove. In particular, combined administration of inositol, alpha lactalbumin and folic acid may comprise administration of about 2000 mg myo-inositol, about 50 mg human alpha lactalbumin and about 200 µg folic acid. In a further especially preferred embodiment, combined administration of inositol, alpha lactalbumin and folic acid may comprise combined administration of 2000 mg myoinositol, 50 mg human alpha lactalbumin and 200 µg folic acid. In particular, combined administration of inositol, alpha lactalbumin and folic acid may comprise administration of about 2000 mg myoinositol, about 50 mg bovine alpha lactalbumin and about 200 µg folic acid. In a further especially preferred embodiment, combined administration of inositol, alpha lactalbumin and folic acid may comprise combined administration of 2000 mg myoinositol, 50 mg bovine alpha lactalbumin and 200 µg folic acid.

In an especially preferred embodiment of the medical uses and therapeutic methods set out above, the inositol and alpha lactalbumin are administered in combination in the form of a composition comprising inositol and alpha lactalbumin, and optionally also a source of folate, preferably folic acid. Combined administration of inositol and alpha lactalbumin, optionally together with a source of folate, preferably folic acid, in a composition presupposes that the inositol and alpha lactalbumin, and optionally the source of folate, preferably folic acid, are administered simultaneously and by the same route. In an especially preferred embodiment, the composition is a composition according to the invention as set out hereinabove, e.g. a composition comprising inositol and alpha lactalbumin, wherein inositol and alpha lactalbumin are present in a respective weight ratio of about 1:1-50:1, between 1:1-50:1, about 8:1-50:1, between 8:1-50:1, about 30:1-50:1, between 30:1-50:1, about 33:1-43:1, between 33:1-43:1, about 40:1 or any other preferred inositol:alpha lactalbumin weight ratio disclosed in any other embodiment associated with the inventive composition described hereinabove. Any embodiment of the inventive composition as set out hereinabove may be used in the inventive medical uses and methods of treatment set out hereinabove, and is herewith disclosed in that context, in particular in relation to the various weight ratios between inositol:alpha lactalbumin. In particular, the inositol and alpha lactalbumin administered in the composition may be in a respective inositol:alpha lactalbumin weight ratio of about 40:1, optionally together with a source of folate, preferably folic acid, in a respective alpha lactalbumin: folate source weight ratio of about 1:0.004. In this embodiment, the inositol is preferably myoinositol and the alpha lactalbumin is preferably human or bovine alpha lactalbumin. In an especially preferred embodiment, the medical uses and methods of treatment hereinabove comprise combined administration of about 2000 mg of myoinositol, about 50 mg of human or bovine alpha lactalbumin and, optionally, about 200 µg of folic acid in a single composition formulated for oral delivery, e.g. in the form of a tablet, including but not limited to an effervescent tablet, a powder (e.g. in the form of a sachet), a hard capsule, a soft gel capsule, a syrup, a cachet, a troche, or a lozenge. In an especially preferred embodiment, the medical uses and methods of treatment hereinabove comprise combined administration of about 2000 mg of myoinositol, about 50 mg of human or bovine alpha lactalbumin and, optionally, about 200 µg of folic acid in a powder (e.g. in the form of a sachet) or a soft gel capsule. In a further especially preferred embodiment, the medical uses and methods of treatment hereinabove comprise combined administration of about 2000 mg of myoinositol, about 50 mg of human or bovine alpha lactalbumin and, about 200 µg of folic acid in a powder (e.g. in the form of a sachet) or a soft gel capsule.

Kits

A further aspect of the invention relates to a kit, e.g. a kit of parts, comprising inositol in a first container and alpha lactalbumin in a second container. The inositol in the first container may be any of the inositol or inositol mixtures set out hereinabove, in particular myoinositol, D-chiro inositol or a mixture of myoinositol and D-chiro inositol in any weight ratio. In particular, a mixture of myoinositol and D-chiro inositol in the first container may be in any weight ratio as set out hereinabove. Similarly, the alpha lactalbumin in the second container may be human or bovine alpha lactalbumin.

Both the inositol and the alpha lactalbumin in the respective first and second containers of the kit may be formulated for any type of administration, as set out hereinabove. The routes of administration for which the inositol and alpha lactalbumin in the respective first and second containers of the kit may be formulated may be the same or different. In the event that the routes of administration for which the inositol and alpha lactalbumin in the respective first and second containers of the kit are formulated are the same, it is preferred that the route of administration is oral. In this case, the inositol and alpha lactalbumin in the respective first and second containers of the kit may be independently formulated as a tablet, including but not limited to an effervescent or multilayer tablet, a powder (e.g. in the form of a sachet), a hard capsule, a soft gel capsule, a syrup, a cachet, a troche, or a lozenge, or a liquid preparation. Independent formulation of each of inositol and alpha lactalbumin as a tablet, powder or soft gel capsule is preferred, with formulation of each of inositol and alpha lactalbumin in either powder or soft gel form being especially preferred.

The kit may additionally comprise information related e.g. to the content and dosing of each of the kit components. This information may be in the form of a printed message on the outside of a box comprising the kit, in the form of a leaflet comprised inside a box containing the kit, or in the form of a printed internet address referring to a webpage providing information, or further information, relating e.g. to the contents, intended use, dosing or administration regimen of the kit contents, or any mixture thereof.

The amount of inositol and alpha lactalbumin in the respective containers of the kit may be in any of the inositol:alpha lactalbumin weight ratios set out hereinabove. Further, the inositol in the first container may be myoinositol, D-chiro-inositol or any mixture thereof in any ratio, especially any of the myoinositol:D-chiro-inositol weight ratios set out hereinabove.

In one embodiment the kit further comprises a source of folate, preferably folic acid, which may be comprised in the first container, in the second container, in both the first container and the second container, in a third container or in any combination thereof. The source of folate is as defined as set out hereinabove, and is preferably folic acid.

Food and Drink Products

In a further aspect, the present invention relates to a food or drink product comprising inositol and alpha lactalbumin in which the weight ratio of inositol to alpha lactalbumin (inositol:alpha lactalbumin) is about 1:1-50:1. This means that the amount by weight of inositol in the food product or drink product will be greater than the amount by weight of alpha lactalbumin in the food product or drink product. The inositol may be any of the inositol or inositol mixtures set out hereinabove, in particular myoinositol, D-chiro inositol or a mixture of myoinositol and D-chiro inositol in any weight ratio. In particular, a mixture of myoinositol and D-chiro inositol may be in any weight ratio as set out hereinabove. Similarly, the alpha lactalbumin may be human or bovine alpha lactalbumin.

As used herein, the term "food product" refers to an ingestible substance which, at the temperature it is properly stored and ingested, is in a solid or semi solid form, and which will be chewed prior to swallowing.

As used herein, the term "drink product" refers to an ingestible substance which, at the temperature it is properly stored and ingested, is in a free-flowing liquid form, and which will not be chewed prior to swallowing.

The food product may in principle be any food product which has been processed to comprise both inositol and alpha lactalbumin in the specified ratio. Examples of such food products include a food bar, such as a chocolate bar, granola bar, ice cream bar or energy bar; chewing gum; candy; a breath mint; yogurt; an edible gel; a ready-made meal, for example a freeze-dried ready-made meal; a spread; a pudding; or a processed fruit product such as a fruit rollup or a fruit stick. Examples of such drink products include fruit juice or fruit juice-containing drinks, dairy product drinks, e.g. milk-containing drinks or buttermilk-containing drinks, whey-containing drinks and yogurt-containing drinks, energy drinks, soft drinks, flavored water drinks etc.

The food or drink product may comprise inositol and alpha lactalbumin in any of the respective weight ratios set out hereinabove. For example, the food or drink product may comprise inositol and alpha lactalbumin in a respective (inositol:alpha lactalbumin) weight ratio of between 1:1 and 50:1, about 2:1-50:1, between 2:1 and 50:1, about 3:1-50:1, between 3:1 and 50:1, about 4:1-50:1, between 4:1 and 50:1, about 5:1-50:1, between 5:1 and 50:1, about 6:1-50:1, between 6:1 and 50:1, about 7:1-50:1, between 7:1 and 50:1, about 8:1-50:1, between 8:1 and 50:1, about 30:1-50:1, between 30:1 and 50:1, about 33:1-43:1, between 33:1 and 43:1, about 40:1 or any other preferred inositol:alpha lactalbumin weight ratio disclosed in any other embodiment associated with other aspects of the invention hereinabove.

The food or drink product may comprise a minimum amount of inositol, a minimum amount of alpha lactalbumin, or a minimum amount of both inositol and alpha lactalbumin as set out hereinabove. For example, the food or drink product in which the weight ratio of inositol to alpha lactalbumin (inositol:alpha lactalbumin) is about 1:1-50:1, or is any other weight ratio as set out above, may comprise as much as about 6000 mg inositol, about 500-4000 mg inositol, about 1000-3000 mg inositol or about 600 mg or about 2000 mg of inositol. Similarly, the food or drink product in which the weight ratio of inositol to alpha lactalbumin (inositol:alpha lactalbumin) is about 1:1-50:1 may comprise about 10-500 mg alpha lactalbumin, about 20-100 mg alpha lactalbumin, about 30-70 mg alpha lactalbumin or about 50 mg alpha lactalbumin. Ideally, the food product or drink product will be presented as a discrete ingestible unit, so that ingestion of one unit of the food product, e.g. one food bar, or one unit of the drink product, e.g. one bottle of drink, will provide a minimum amount of inositol and alpha lactalbumin which, alone or combined with ingestion of further discrete edible units, will support any of the therapeutic aims indicated hereinabove.

In a further embodiment, the food or drink product may further comprise a source of folate, preferably folic acid, which is defined as set out hereinabove.

In one particularly preferred embodiment, the food or drink product comprises about 2000 mg myoinositol and about 50 mg of human or bovine alpha lactalbumin, and may additionally comprise about 200 µg of folic acid.

The following provides several examples illustrating various embodiments of the present invention, and the technical effects and advantages which it achieves. It should be understood that the following examples are presented for illustrative purposes only, and do not limit the claimed invention. Indeed, the skilled person will readily be able to realize other embodiments within the spirit and scope of the claimed invention while achieving the describes technical advantages.

EXAMPLES

General

In the broadest sense, the present inventors have found that a combined administration of inositol, e.g. myoinositol, and alpha lactalbumin, e.g. alpha lactalbumin, achieves ovulation in women with PCOS in whom ovulation could not be achieved by administration of inositol, e.g. myoinositol alone. The combination of inositol and alpha lactalbumin, e.g. myoinositol and alpha lactalbumin, in a regimen for preventing or treating PCOS in female subjects in need thereof therefore allows the medical practitioner to successfully treat PCOS in cases previously recalcitrant to existing PCOS treatment. The ultimate effect of the present invention is thus to expand the population of PCOS patients which may benefit from treatment with inositol, e.g. myoinositol.

The present inventors have further found that a combined administration of inositol, e.g. myoinositol, and alpha lactalbumin, e.g. alpha lactalbumin, achieves biochemical pregnancy in women with idiopathic infertility, in whom biochemical pregnancy could not be achieved by administration of inositol, e.g. myoinositol alone. The combination of inositol and alpha lactalbumin, e.g. myoinositol and alpha lactalbumin, in a regimen for preventing or treating idiopathic infertility in female subjects in need thereof therefore allows the medical practitioner to successfully treat idiopathic infertility. The ultimate effect of the present invention is thus to expand the population of idiopathic infertility patients which may benefit from treatment with inositol, e.g. myoinositol.

While not wanting be bound by theory, the observed results suggest that the improved absorption of myoinositol when administered in combination, e.g. in the same composition as, alpha lactalbumin may be related to a beneficial change in gut microbiota and/or a carrier effect, both effected by alpha lactalbumin.

Example 1

Pharmacokinetic Evaluation in Healthy Subjects: Myoinositol Plus Alpha Lactalbumin The present example describes a pharmacokinetic study combining the oral administration of myoinositol and alpha lactalbumin in healthy subjects. The study aims to determine whether the combination of myoinositol and alpha lactalbumin is able to increase the plasma level of myoinositol above that observed after administering myoinositol alone.

The study involved 15 healthy volunteers, 6 men and 9 women. Subjects were evaluated based on medical history, physical examination and laboratory screenings, and subjects who were in poor general health were excluded. Volunteers were aged between 18 and 35 years, with a body mass index (BMI) ranging between 21 and 25 kg/m$^2$.

Subjects received orally 6 g of myoinositol in powder form and then, after a washout period of 7 days, 6 g of myoinositol and 150 mg alpha lactalbumin, also in powder form. Pharmacokinetic (PK) parameters were evaluated following respective administrations of myoinositol alone or in combination with alpha lactalbumin, in each case determining the concentration of myoinositol in the plasma at various time points following a respective administration. Blood samples were collected by venous puncture at pre-dose (time point 0), and at time points 30, 60, 90, 120, 180 and 300 min post-administration.

As indicated above, the study consisted of two different phases:

Phase I: 6 g of myoinositol in powder form was administered

Phase II: 6 g of myoinositol +150 mg alpha lactalbumin in powder form was administered The two phases were separated by a washout period of seven days.

Quantification of myoinositol was performed using gas chromatography-mass spectrometry (GCMS) analysis after extraction with organic solvent (methanol) and derivatization with 500 µL of metoxamin in pyridine for 30 min at 70° C.

Cmax and Tmax were obtained directly from the plasma concentration, while the area under the curve (AUC(0-300)) was calculated by the trapezoidal method over the time span of 0 to 300 min (Purves A., Journal of Pharmacokinetics and Biopharmaceutics, 1992; 20 (3), 211-224). Data sets were compared using a t-test and a p value <0.05 was considered statistically significant.

TABLE 1

Pharmacokinetic parameters after oral administration of 6 g of myoinositol in powder and 6 g of myoinositol plus 150 mg alpha lactalbumin in powder.

| Parameter | Mean (SD) myoinositol 6 g | Mean (SD) myoinositol 6 g + alpha lactalbumin 150 mg | Δ % | p-value |
|---|---|---|---|---|
| Cmax (µmol/l) | 98.00 (7) | 127.0 (10) | 29% | p <0.0001 |
| Tmax (min) | 180.0 (8) | 180.0 (5) | 0% | Not significant |
| AUC (0-300) | 23760 (3568) | 29370 (4793) | 24% | p <0.001 |

All the enrolled subjects completed the trial. The analysis of myoinositol plasma concentrations measured yielded interesting results regarding the PK parameters of the two formulations, with respect to the resulting plasma concentration of myoinositol. Data showed myoinositol plasma concentration resulting from the two phases of the study (Table 1). The data obtained are graphically depicted in FIG. 1 for the 2 phases of the study. As the above data indicate, and as can clearly be seen in corresponding FIG. 1, myoinositol plasma concentrations after administration of powder containing 6 g of myoinositol and alpha lactalbumin were significantly higher than after administration of 6 g of myoinositol powder alone. These results show that administering myoinositol in combination with alpha lactalbumin leads to a significantly higher plasma concentration of myoinositol than observed when administering myoinositol alone.

Example 2

Pharmacokinetic evaluation in healthy subjects: glucose plus alpha lactalbumin

The present study aims to determine whether the effect observed in Example 1 is specific to the combination of inositol and alpha lactalbumin, e.g. myoinositol and alpha lactalbumin. In order to evaluate this, the present inventors performed a study using glucose rather than inositol (as polyols/carbohydrates, glucose and inositol have similar structures and the same molecular weight). Specifically, glucose was administered to subjects alone, as well as in combination with alpha lactalbumin to see whether alpha lactalbumin increases the bioavailability of glucose in a manner similar to that observed in Example 1 above for myoinositol.

The study involved 10 healthy volunteers, 5 men and 5 women. Subjects were evaluated based on medical history, physical examination and laboratory screenings, and subjects who were in poor general health were excluded. Volunteers were aged between 18 and 35 years, with a body mass index (BMI) ranging between 21 and 25 kg/m$^2$.

Subjects received orally a 50% solution of glucose (100 ml) and then, after a washout period of 7 days, the same solution plus 1200 mg of alpha lactalbumin. In order to ensure comparability with the results of Example 1 above, the 50% glucose solution contained 50 g glucose, and this amount was combined with 1200 mg of alpha lactalbumin. This yielded about same ratio for glucose:alpha lactalbumin as used in for myoinositol: alpha lactalbumin in Example 1. Pharmacokinetic (PK) parameters were evaluated following respective administrations of glucose alone or in combination with alpha lactalbumin, in each case determining the concentration of glucose in the blood at various time points following a respective administration. Blood samples were collected by capillary puncture at pre-dose (time point 0), and at time points of 30, 60, 120, and 180 min post-administration.

As indicated above, the study consisted of two different phases:

Phase I: 50% solution of glucose (100 ml) was administered.

Phase II: 50% solution of glucose (100 ml) +1200 mg alpha lactalbumin in tablet form was administered (by the same route; a tablet of alpha lactalbumin was swallowed simultaneously with the glucose solution).

The two phases were separated by a washout period of seven days.

Glucose quantification was performed using a glucometer Accu-Chek Active (Roche Diabetes Care GmbH). Cmax and Tmax were obtained directly from the blood concentration, while the area under the curve (AUC(0-180)) was calculated by the trapezoidal method over the time span of 0 to 180 min (Purves A., Journal of Pharmacokinetics and Biopharmaceutics, 1992; 20 (3), 211-224). Data sets were compared using a t-test and a p value <0.05 was considered statistically significant.

TABLE 2

Pharmacokinetic parameters after oral administration of a 50% glucose solution and 50% glucose solution plus 1200 mg alpha lactalbumin in tablet.

| Parameter | Mean (SD) sol 50% Glu | Mean (SD) sol 50% glu + alpha lactalbumin 1200 mg | Δ % | p-value |
|---|---|---|---|---|
| Cmax (mg/dl) | 159.01 (21) | 151.67 (32) | -5% | Not significant |
| Tmax (min) | 30.6 (12) | 30.2 (7) | 0% | Not significant |
| AUC (0-180) | 21141 (153) | 20555 (278) | -3% | Not significant |

Results did not show any significant difference in the glucose blood levels in the two groups (Table 2). Indeed, no statistical difference has been shown between the two AUCs. This indicates that alpha lactalbumin has no appreciable effect on another compound very similar to myoinositol, suggesting that the advantageous effect observed for the combined administration of myoinositol and alpha lactalbumin is specific to that pair of substances.

Example 3

Clinical Evaluation on PCOS Women

The present study aims to develop an efficacious therapy in women suffering from PCOS based on the improved absorption of inositol, e.g. myoinositol, when administered in combination with alpha lactalbumin. Specifically, while treatment of PCOS with myoinositol alone correlates to an improvement in the disease in a significant number of women, there remain women who still fail to respond to treatment with myoinositol alone. The present inventors thus sought to determine whether the higher level of myoinositol absorption observed when administering myoinositol together with alpha lactalbumin might allow successful treatment of PCOS patients who had previously not responded to treatment with myoinositol alone. If so, then the treatment of PCOS with inositol in combination with alpha lactalbumin, e.g. myoinositol in combination with alpha lactalbumin, would represent a significant therapeutic advance, allowing treatment of PCOS in previously recalcitrant cases, thereby substantially extending the therapeutic benefit of inositol, e.g. myoinositol, in treating PCOS.

The present study included 20 anovulatory PCOS patients.

Inclusion criteria were: age 20-35 years; PCOS according to Rotterdam ESHRE-ASRM consensus workshop group; anovulation and infertility >1 year. Indeed, according to Rotterdam criteria, PCOS was diagnosed performed if 2 out of the 3 following factors were fulfilled: a) oligo- or anovulation, b) clinical and/or biochemical signs of hyperandrogenism, and c) polycystic ovaries.

Patients were excluded in the event of other conditions causing ovulatory dysfunction, such as hyperprolactinemia or hypothyroidism, or androgen excess, such as adrenal hyperplasia or Cushing's syndrome, and also in the case of intake of other drugs that can potentially influence ovulation.

All the patients were given myoinositol (Inofolic®, Lo.Li. Pharma, Rome, Italy), containing 2 g myoinositol and 0.2 mg folic acid in dose of two sachets per day before meals, in order to induce ovulation.

Folic acid was included in the formulation considering that all women enrolled were of childbearing age who have tried unsuccessfully to become pregnant. Folic acid supplementation is indeed suggested in case pregnancy occurs. However, as discussed hereinabove, folic acid is not itself necessary for the observed therapeutic effect. Indeed, several controlled clinical trials relating to the treatment of PCOS have been carried out using folic acid as placebo and determined that no specific effect attributable to folic acid was found in the selected population (see e.g. Costantino D, Minozzi G, Minozzi E, Guaraldi C. Metabolic and hormonal effects of myo-inositol in women with polycystic ovary syndrome: a double-blind trial. Eur Rev Med Pharmacol Sci 2009; 13:105-10; Genazzani A D, Lanzoni C, Ricchieri F, Jasonni V M. Myo-inositol administration positively affects hyperinsulinemia and hormonal parameters in overweight patients with polycystic ovary syndrome. Gynecol Endocrinol. 2008; 24:139-44; and Gerli S, Papaleo E, Ferrari A, Di Renzo GC. Randomized, double blind placebo-controlled trial: effects of myo-inositol on ovarian function and metabolic factors in women with PCOS. Eur Rev Med Pharmacol Sci 2007; 11:347-54). Accordingly, the technical effect described herein relating to the treatment of infertility or subfertility, in particular infertility or subfertility caused by PCOS or anovulation, as well as relating to the treatment of PCOS or anovulation itself, can be achieved with inositol and alpha lactalbumin in dual combination alone, without a folate source, e.g. folic acid.

Ovulation was assessed using ultrasound examination on days 12, 14 and 20 of the cycle. Treatment was performed for three months.

The characteristics of the study participants are shown in Table 3.

TABLE 3

| Baseline characteristics of enrolled patients (n = 20) | |
|---|---|
| Age (years) | 27 ± 4 |
| Height (cm) | 165.2 ± 5.6 |
| Weight (kg) | 72.0 ± 14.3 |
| BMI (kg/m2) | 26.5 ± 5.5 |

Data presented as mean ± SD

Following myoinositol treatment, 13 of the 20 women (65%) ovulated, while 7 (35%) were resistant and did not ovulate. Thus, in the present study, 7 of the original 20 women suffering from PCOS (35%) failed to respond to treatment with myoinositol alone. These 7 non-responders then became the subject of a second phase of the study, in which they received treatment with myoinositol in combination with alpha lactalbumin.

Specifically, myoinositol plasma levels were tested in these non-responding patients; a mean value of 17±3.5 µmol/l myoinositol was observed. Successively, a treatment with 2 g myoinositol, 0.2 mg folic acid and 50 mg alpha lactalbumin was performed in doses of two powder sachets per day before meals during the next three months. Of the 7 myoinositol resistant patients after combined treatment with myoinositol and alpha lactalbumin, 5 of the original non-responders (i.e. 71% of the original non-responders) ovulated. Myoinositol plasma levels at the end of the treatment were significantly higher than baseline (35±3.8 µmol/l versus 17±3.5 µmol/l, the latter having been measured at the beginning of the second phase of the study) and were comparable to those patients who responded positively to treatment with myoinositol alone (38 µmol/l). The data obtained in this study are shown below in Table 4.

TABLE 4

Mean myoinositol plasma concentration and ovulation results in 7 patients non-responsive to myoinositol treatment.

| | MYOINOSITOL PLASMA LEVELS | | OVULATION |
|---|---|---|---|
| TREATMENTS | T0 mean µmol/l (±SD) | T3 mean µmol/l (±SD) | T3 (number of patients) |
| 3 months myoinositol treatment | — | 17 (3.5) | 0 |
| 3 (further) months myoinositol + alpha lactalbumin treatment | 17 (3.5) | 35 (3.8) | 5 |

As the above results clearly indicate, combination of alpha lactalbumin with inositol, e.g. myoinositol, in the treatment of PCOS allows a significant improvement in the treatment of PCOS patients who would be otherwise resistant to treatment with myoinositol alone. Specifically, a full 71% of the patients who were otherwise resistant to treatment with myoinositol alone, and who would have continued to suffer from anovulation and its attendant infertility following treatment with myoinositol alone, were caused to ovulate by combining myoinositol with alpha lactalbumin. The combination of alpha lactalbumin with myoinositol thus represents a significant improvement in the treatment of PCOS, thus reestablishing ovulation and greatly increasing the chances of a desired pregnancy in many women who would otherwise have remained infertile. The data of the above experiment strongly suggest that this improvement is due to the ability of alpha lactalbumin to significantly increase absorption of inositol, e.g. myoinositol, effectively increasing the amount of myoinositol available in the blood to exert a beneficial effect.

Example 4

Clinical Evaluation on Women Affected by Idiopathic Infertility

The present study aims to develop an efficacious therapy in women suffering from idiopathic infertility based on the improved absorption of inositol, e.g. myoinositol, when administered in combination with alpha lactalbumin. Specifically, while treatment of idiopathic infertility with myoinositol alone correlates to an improvement in the disease in a significant number of women, there remain women who still fail to respond to treatment with myoinositol alone. The present inventors thus sought to determine whether the higher level of myoinositol absorption observed when administering myoinositol together with alpha lactalbumin might allow successful treatment of idiopathic infertility patients who had previously not responded to treatment with myoinositol alone. If so, then the treatment of idiopathic infertility with inositol in combination with alpha lactalbumin, e.g. myoinositol in combination with alpha lactalbumin, would represent a significant therapeutic advance, allowing treatment of idiopathic infertility in previously recalcitrant cases, thereby substantially extending the therapeutic benefit of inositol, e.g. myoinositol, in treating idiopathic infertility.

The present study included 40 women affected by idiopathic infertility. Inclusion criteria were: women affected by idiopathic infertility as defined below, aged 30-40 years, who were not receiving any therapy with drugs which potentially influence ovulation. Patients were given a thorough evaluation and were tested for a number of diseases, as described in the following. Testing positive for any of these diseases tested sufficed to exclude a patient as being "idiopathically infertile". Specifically, patients were excluded from this trial in the event they were diagnosed positive for any of: hyperprolactinemia, hypothyroidism, Cushing's syndrome, adrenal hyperplasia, obesity, polycystic ovary syndrome (PCOS) or anovulation. The person skilled in the art can routinely diagnose each of the above mentioned conditions. For example, hyperprolactinemia can be diagnosed when serum prolactin levels are found to be over 20 μg/L, as e.g. described in Serri et al., *CMAJ*, 2003, 169(6): 575-581. Hypothyroidism can be diagnosed when the serum TSH level is found to be over 4.5 mIU/L (Garber et al., CLINICAL PRACTICE GUIDELINES FOR HYPOTHYROIDISM IN ADULTS: COSPONSORED BY THE AMERICAN ASSOCIATION OF CLINICAL ENDOCRINOLOGISTS AND THE AMERICAN THYROID ASSOCIATION; *Endocrine Practice* vol. 18 No. 6, 2012). Cushing's syndrome can be diagnosed according to Nieman et al., *J. Clin. Endocrinol. Metab.*, 2008, 93(5): pages 1526-1540. Adrenal hyperplasia can be diagnosed according to Witchel et al., *Int. J. Pediatr. Endocrinol.*, 2010:625105. Obesity can be diagnosed when the body mass index (BMI) is over 30.

"Treatment" of idiopathic infertility, as was performed in the present study, was considered to be the at least temporary amelioration or abolishment of a pathological state in which, despite repeated attempts over an extended time to become pregnant, e.g. about 12 months, no pregnancy has been achieved. The primary readout was the achievement of biochemical pregnancy as assessed using an assay (HCG Combo Card, Shanghai Chemtron Biotech Co., Ltd., catalog.no. 6011C31-4) for beta human chorionic gonadotropin (beta hCG). Biochemical pregnancy was achieved when the sample was positive for beta hCG 14 days after ovulation.

The characteristics of the study participants are shown in Table 5.

TABLE 5

| Baseline characteristics of enrolled patients (n = 40) | |
|---|---|
| Age (years) | 36.1 ± 1.2 |
| BMI (kg/m$^2$) | 24.7 ± 1.3 |

Data presented as mean ± SD

The treatment was performed in 2 phases:

In the first phase, all patients received myoinositol (Inofolic®, Lo.Li. Pharma, Rome, Italy) containing 2 g myoinositol and 0.2 mg folic acid in powder form in a dose of two sachets per day before meals. That means that patients were administered this dose orally twice a day fasting, for a total of for 3 months (Table 6). This treatment allowed the identification of myoinositol-resistant subjects.

In the second phase, patients who did not get pregnant, classified as "myoinositol-resistant subjects", were treated further. They received 2 g myoinositol, 0.2 mg folic acid and 50 mg alpha lactalbumin orally in doses of two powder sachets per day before meals for three months (Table 7).

The results of the present experiment are summarized in Tables 6 and 7, below.

TABLE 6

| First phase of treatment: myoinositol (2 g) for 3 months | | | | |
|---|---|---|---|---|
| Num. patients | Achieving biochemical pregnancy | % | Not achieving biochemical pregnancy | % |
| 40 | 21 | 52.5 | 19 | 47.5 |

Following myoinositol treatment, 21 of the 40 women (52.5%) achieved biochemical pregnancy, while 19 (47.5%) did not achieve biochemical pregnancy. Thus, in the present study, 19 of the original 40 women suffering from idiopathic infertility (47.5%) failed to respond to treatment with myoinositol alone, i.e. without alpha lactalbumin. These 19 "myoinositol-resistant" non-responders then became the subjects of a second phase of the study, in which they received treatment with myoinositol in combination with alpha lactalbumin.

TABLE 7

| Second phase of treatment: myoinositol (2 g) and alpha lactalbumin (50 mg) for 3 months | | | | |
|---|---|---|---|---|
| Num. patients ins. resist. | Achieving biochemical pregnancy | % | Not achieving biochemical pregnancy | % |
| 19 | 12 | 63.2 | 7 | 36.8 |

Following treatment with myoinositol in combination with alpha lactalbumin, 12 of the 19 "myoinositol-resistant" women (63.2% of that group) achieved biochemical pregnancy, while 7 (36.8% of that group) did not achieve biochemical pregnancy.

The administration of a combination of myoinositol with alpha lactalbumin overcame many cases of inositol resistance, obtaining a success of the therapy and increasing the chance of becoming biochemically pregnant from 52.5% (21 out of 40 women in phase 1) to 82.5% overall (33 out of 40 women becoming pregnant in combined phases 1 and 2). As outlined above in Example 3 in the context of treating PCOS, equivalent considerations with regard to the presence of a folate source in the composition also apply in the present context of treating infertility having its origin in idiopathic infertility, and in the context of treating idiopathic infertility itself. In particular, the technical effect described herein relating to the treatment of infertility having its origin in idiopathic infertility, as well as relating to the treatment of idiopathic infertility itself, can be achieved with inositol and alpha lactalbumin in dual combination alone, without a folate source, e.g. folic acid.

As the above results clearly indicate, combination of alpha lactalbumin with inositol, e.g. myoinositol, in the treatment of idiopathic infertility allows a significant improvement in the treatment of idiopathic infertility patients who would otherwise remain resistant to treatment with myoinositol alone ("myoinositol-resistant" women). Specifically, 63.2% of the patients who were otherwise resistant to treatment with myoinositol alone, and who would have continued to suffer from idiopathic infertility following treatment with myoinositol alone, became biochemically pregnant by combining myoinositol with alpha lactalbumin. The combination of alpha lactalbumin with myoinositol thus represents a significant improvement in the treatment of idiopathic infertility, thus greatly increasing the chances of a desired pregnancy in many women who would otherwise have remained infertile.

The invention claimed is:

1. A composition comprising inositol and alpha lactalbumin, wherein the inositol and the alpha lactalbumin are present in a respective weight ratio of about 33:1-43:1.

2. The composition of claim 1, wherein the inositol is chosen from myoinositol, D-chiroinositol or a mixture thereof in any weight ratio.

3. The composition of claim 1, wherein the composition comprises
about 500-4000 mg inositol;
about 1000-3000 mg inositol;
about 2000 mg inositol;
about 10-500 mg alpha lactalbumin;
about 20-100 mg alpha lactalbumin;
about 30-70 mg alpha lactalbumin; or
about 50 mg alpha lactalbumin.

4. The composition of claim 1, wherein the composition comprises about 2000 mg myoinositol and about 50 mg alpha lactalbumin.

5. The composition of claim 1, wherein the composition additionally comprises a folate.

6. A method of treating or preventing infertility, subfertility, polycystic ovary syndrome (PCOS), anovulation or idiopathic infertility in a subject, wherein the method comprises administering inositol to the subject in combination with alpha lactalbumin.

7. The method of claim 6, wherein the infertility or subfertility is infertility or subfertility caused by polycystic ovary syndrome (PCOS) or anovulation or wherein the infertility has its origin in idiopathic infertility.

8. The method of claim 6, wherein the method comprises administering the inositol and the alpha lactalbumin to the subject non-simultaneously within a given combined administration of a given regimen.

9. The method of claim 6, wherein the method comprises administering the inositol to the subject simultaneously with alpha lactalbumin.

10. The method of claim 6, wherein the method comprises administering the combination of inositol and alpha lactalbumin in a respective weight ratio of about 1:1-50:1, about 8:1-50:1, about 30:1-50:1, about 33:1-43:1 or about 40:1.

11. The method of claim 10, wherein the method comprises administering to the subject
about 500-4000 mg inositol;
about 1000-3000 mg inositol;
about 2000 mg inositol;
about 10-500 mg alpha lactalbumin;
about 20-100 mg alpha lactalbumin;
about 30-70 mg alpha lactalbumin; or
about 50 mg alpha lactalbumin.

12. The method of claim 6, wherein the inositol is chosen from myoinositol, D-chiroinositol or a mixture thereof in any weight ratio.

13. The method of claim 6, wherein the method further comprises administering a folate to the subject in combination with inositol and alpha lactalbumin.

14. A kit comprising a composition of claim 1.

15. A food product or drink product comprising the composition of claim 1.

16. The food product or drink product of claim 15, wherein the food product or drink product comprises inositol and alpha lactalbumin in a respective weight ratio of about 40:1.

17. The food product or drink product of claim 15, wherein the food product or drink product comprises
   about 500-4000 mg inositol;
   about 1000-3000 mg inositol;
   about 2000 mg inositol
   about 10-500 mg alpha lactalbumin;
   about 20-100 mg alpha lactalbumin;
   about 30-70 mg alpha lactalbumin; or
   about 50 mg alpha lactalbumin.

18. The food product or drink product of claim 15, wherein the food product or drink product comprises about 2000 mg myoinositol and about 50 mg alpha lactalbumin.

19. The composition of claim 5, where in the folate is folic acid.

20. The method of claim 13, wherein the folate is folic acid.

* * * * *

UNITED STATES PATENT AND TRADEMARK OFFICE
CERTIFICATE OF CORRECTION

PATENT NO. : 11,364,282 B2
APPLICATION NO. : 16/647715
DATED : June 21, 2022
INVENTOR(S) : Unfer Page 1 of 1

It is certified that error appears in the above-identified patent and that said Letters Patent is hereby corrected as shown below:

In the Claims

In Column 57, Line 59, Claim 6 should read:
--6. A method of treating or preventing infertility, subfertility, polycystic ovary syndrome (PCOS), anovulation or idiopathic infertility in a subject, wherein the method comprises administering a composition of claim 1.--

In Column 58, Line 43, Claim 10 should read:
--10. The method of claim 6, wherein the method comprises administering the combination of inositol and alpha lactalbumin in a respective weight ratio of about 40:1.--

Signed and Sealed this
Twenty-seventh Day of September, 2022

Katherine Kelly Vidal
*Director of the United States Patent and Trademark Office*

SEQUENCE LISTING

```
<160> NUMBER OF SEQ ID NOS: 12

<210> SEQ ID NO 1
<211> LENGTH: 142
<212> TYPE: PRT
<213> ORGANISM: Homo sapiens

<400> SEQUENCE: 1

Met Arg Phe Phe Val Pro Leu Phe Leu Val Gly Ile Leu Phe Pro Ala
1               5                   10                  15

Ile Leu Ala Lys Gln Phe Thr Lys Cys Glu Leu Ser Gln Leu Leu Lys
            20                  25                  30

Asp Ile Asp Gly Tyr Gly Gly Ile Ala Leu Pro Glu Leu Ile Cys Thr
        35                  40                  45

Met Phe His Thr Ser Gly Tyr Asp Thr Gln Ala Ile Val Glu Asn Asn
    50                  55                  60

Glu Ser Thr Glu Tyr Gly Leu Phe Gln Ile Ser Asn Lys Leu Trp Cys
65                  70                  75                  80

Lys Ser Ser Gln Val Pro Gln Ser Arg Asn Ile Cys Asp Ile Ser Cys
                85                  90                  95

Asp Lys Phe Leu Asp Asp Asp Ile Thr Asp Asp Ile Met Cys Ala Lys
            100                 105                 110

Lys Ile Leu Asp Ile Lys Gly Ile Asp Tyr Trp Leu Ala His Lys Ala
        115                 120                 125

Leu Cys Thr Glu Lys Leu Glu Gln Trp Leu Cys Glu Lys Leu
    130                 135                 140

<210> SEQ ID NO 2
<211> LENGTH: 742
<212> TYPE: DNA
<213> ORGANISM: Homo sapiens

<400> SEQUENCE: 2
atttcaggtt cttgggggta gccaaaatga ggttctttgt ccctctgttc ctggtgggca      60
tcctgttccc tgccatcctg gccaagcaat tcacaaaatg tgagctgtcc cagctgctga     120
```

```
aagacataga tggttatgga ggcatcgctt tgcctgaatt gatctgtacc atgtttcaca    180
ccagtggtta tgacacacaa gccatagttg aaaacaatga agcacggaa tatggactct    240 tccagatcag taataagctt tggtgcaaga gcagccaggt ccctcagtca aggaacatct    300
gtgacatctc ctgtgacaag ttcctggatg atgacattac tgatgacata atgtgtgcca    360
agaagatcct ggatattaaa ggaattgact actggttggc ccataaagcc ctctgcactg    420
agaagctgga acagtggctt tgtgagaagt tgtgagtgtc tgctgtcctt ggcacccctg    480
cccactccac actcctggaa tacctcttcc ctaatgccac ctcagtttgt ttctttctgt    540
tcccccaaag cttatctgtc tctgagcctt gggccctgta gtgacatcac cgaattcttg    600
aagactattt ccagggatg cctgagtggt gcactgagct ctagacccctt actcagtgcc    660 ttcgatggca ctttcactac agcacagatt tcacctctgt cttgaataaa ggtcccactt    720
tgaagtcaaa aaaaaaaaaa aa                                             742

<210> SEQ ID NO 3
<211> LENGTH: 142
<212> TYPE: PRT
<213> ORGANISM: Bos taurus

<400> SEQUENCE: 3

Met Met Ser Phe Val Ser Leu Leu Val Gly Ile Leu Phe His Ala
1               5                   10                  15

Thr Gln Ala Glu Gln Leu Thr Lys Cys Glu Val Phe Arg Glu Leu Lys
            20                  25                  30

Asp Leu Lys Gly Tyr Gly Gly Val Ser Leu Pro Glu Trp Val Cys Thr
        35                  40                  45

Thr Phe His Thr Ser Gly Tyr Asp Thr Gln Ala Ile Val Gln Asn Asn
    50                  55                  60

Asp Ser Thr Glu Tyr Gly Leu Phe Gln Ile Asn Asn Lys Ile Trp Cys
65                  70                  75                  80

Lys Asp Asp Gln Asn Pro His Ser Ser Asn Ile Cys Asn Ile Ser Cys
                85                  90                  95

Asp Lys Phe Leu Asp Asp Asp Leu Thr Asp Asp Ile Met Cys Val Lys
            100                 105                 110

Lys Ile Leu Asp Lys Val Gly Ile Asn Tyr Trp Leu Ala His Lys Ala
        115                 120                 125

Leu Cys Ser Glu Lys Leu Asp Gln Trp Leu Cys Glu Lys Leu
    130                 135                 140

<210> SEQ ID NO 4
<211> LENGTH: 724
<212> TYPE: DNA
<213> ORGANISM: Bos taurus

<400> SEQUENCE: 4
atttcagaat cttgggggt aaccaaaatg atgtcctttg tctctctgct cctggtaggc     60
atcctattcc atgccaccca ggctgaacag ttaacaaaat gtgaggtgtt ccgggagctg    120
aaagacttga agggctacgg aagtgtcagt ttgcctgaat gggtctgtac cacgtttcat    180
accagtggtt atgacacaca agccatagta caaacaatg acagcacaga atatggactc    240
ttccagataa ataataaaat ttggtgcaaa gacgaccaga accctcactc aagcaacatc    300
tgtaacatct cctgtgacaa gttcctggat gatgatctta ctgatgacat tatgtgtgtc    360
aagaagattc tggataaagt aggaattaac tactggttgg cccataaagc actctgttct    420
```

```
gagaagctgg atcagtggct ctgtgagaag ttgtgaacac ctgctgtctt tgctgcttct    480
gtcctctttc tgttcctgga actcctctgc cccgtggcta cctcgttttg cttctttgta    540
ccccccttgaa gctaactcgt ctctgagccc tgggccctgt agtgacaatg gacatgtaag    600
gactaatctc caggggtgca tgaatggcgc tctggacttt tgacccttss tcgatgtccc    660
tgatggcgct tttaatgcaa cagtacatat tccacttttg tcccgaataa aaagcctgat    720
tttg                                                                724
```

<210> SEQ ID NO 5
<211> LENGTH: 142
<212> TYPE: PRT
<213> ORGANISM: Ovis aries

<400> SEQUENCE: 5

```
Met Met Ser Phe Val Ser Leu Leu Val Gly Ile Leu Phe His Ala
1               5                   10                  15

Thr Gln Ala Glu Gln Leu Thr Lys Cys Glu Ala Phe Gln Lys Leu Lys
            20                  25                  30

Asp Leu Lys Asp Tyr Gly Gly Val Ser Leu Pro Glu Trp Val Cys Thr
        35                  40                  45

Ala Phe His Thr Ser Gly Tyr Asp Thr Gln Ala Ile Val Gln Asn Asn
    50                  55                  60

Asp Ser Thr Glu Tyr Gly Leu Phe Gln Ile Asn Asn Lys Ile Trp Cys
65                  70                  75                  80

Lys Asp Asp Gln Asn Pro His Ser Arg Asn Ile Cys Asn Ile Ser Cys
                85                  90                  95

Asp Lys Phe Leu Asp Asp Asp Leu Thr Asp Asp Ile Val Cys Ala Lys
            100                 105                 110

Lys Ile Leu Asp Lys Val Gly Ile Asn Tyr Trp Leu Ala His Lys Ala
        115                 120                 125

Leu Cys Ser Glu Lys Leu Asp Gln Trp Leu Cys Glu Lys Leu
    130                 135                 140
```

<210> SEQ ID NO 6
<211> LENGTH: 723
<212> TYPE: DNA
<213> ORGANISM: Ovis aries

<400> SEQUENCE: 6

```
ttccaggatc ttagggggta accaaaatga tgtccttttgt ctctctgctc ctggtaggca    60
tcctattcca tgccacccag gctgaacaat taacaaaatg tgaggcgttc cagaagctga    120
aggacttgaa ggactacgga ggtgtcagtt tgcctgaatg ggtctgtacc gcatttcata    180
ccagtggtta tgacacacaa gccatagtac aaaacaatga cagcacagaa tatggactct    240
tccagataaa taataaaatt tggtgcaaag acgaccagaa ccctcactca aggaacatct    300
gtaacatctc ctgtgacaag ttcctggatg atgatcttac tgatgacatt gtgtgtgcca    360
agaagattct ggataaagta ggaattaact actggttggc ccataaagca ctctgttctg    420
agaagctgga tcagtggctc tgtgagaagt tgtgaacacc tgctgtcttt gctgcttctg    480
ccctctttct gttcctggaa ctcctctgcc ccttggctac ctcgttttgc ttctttgtac    540
ccccttgaag ctaacttgtc tctgagccct gggccctgta gtggcgatgg acatgtaagg    600
actaatctct agggatgcat gaatggtgct cgggacattt gacccttgct cggtgccccc    660
gatagcactt ttaatgcaac agtgcatatt ccacttctgt cctgaataaa aggcctgatt    720
``` ctg                                                                          723

<210> SEQ ID NO 7
<211> LENGTH: 141
<212> TYPE: PRT
<213> ORGANISM: Sus scrofa

<400> SEQUENCE: 7

Met Met Ser Phe Val Ser Leu Leu Val Val Gly Ile Leu Phe Pro Ala
1               5                   10                  15

Ile Gln Ala Lys Gln Phe Thr Lys Cys Glu Leu Ser Gln Val Leu Lys
            20                  25                  30

Asp Met Asp Gly Tyr Gly Asp Ile Thr Leu Pro Glu Trp Ile Cys Thr
        35                  40                  45

Ile Phe His Ile Ser Gly Tyr Asp Thr Lys Thr Ile Val His Asp Asn
    50                  55                  60

Gly Ser Thr Glu Tyr Gly Leu Phe Gln Ile Asn Asn Lys Leu Trp Cys
65                  70                  75                  80

Arg Asp Asn Gln Ile Gln Ser Lys Asn Ile Cys Gly Ile Ser Cys Asp
                85                  90                  95

Lys Phe Leu Asp Asp Asp Leu Thr Asp Asp Met Met Cys Ala Lys Lys
            100                 105                 110

Ile Leu Asp Asn Glu Gly Ile Asp Tyr Trp Leu Ala His Lys Ala Leu
        115                 120                 125

Cys Ser Glu Lys Leu Asp Gln Trp Leu Cys Glu Lys Met
    130                 135                 140

<210> SEQ ID NO 8
<211> LENGTH: 685
<212> TYPE: DNA
<213> ORGANISM: Sus scrofa

<400> SEQUENCE: 8
aaaatgatgt cctttgtctc tctcctcgtg gtggggattc tctttcctgc catccaggcc     60
aagcaattta caaatgtga gctgtcccag gtgctgaaag acatggatgg ctatggagac    120
atcactttgc ctgaatggat ctgtaccata tttcatatca gtggctatga cacaaaaacc    180
attgtgcatg acaatggcag cacagaatat ggactcttcc agatcaataa taaactctgg    240
tgcagagaca accagatcca gtcaaagaac atctgtggca tctcctgtga caaattcctg    300
gatgatgacc ttactgatga catgatgtgt gccaagaaga tcctggataa tgaagggatt    360
gactactggt tggcccataa agcactctgt tcagaaaaac tggatcagtg gctctgtgag    420
aagatgtgaa cacccgctgt cttgctgctt ctgccttctt tatgttcctg gaactcctct    480
tccctaaggc tacctcattt tacttctttg tatcctcttg aagctaattt gtctctctga    540
gccctgggcc ctgtagtgat tgttatccgg acactattct ctagagatgc gtgactggtg    600
cactggattt ttaaccttg ctcagtgccc ctgattggct gtactacaac agtggattca    660
ctgtctgaat aaagggctga tcttg                                          685

<210> SEQ ID NO 9
<211> LENGTH: 142
<212> TYPE: PRT
<213> ORGANISM: Capra hircus

<400> SEQUENCE: 9

Met Met Ser Phe Val Ser Leu Leu Leu Val Gly Ile Leu Phe His Ala

```
1               5                   10                  15
Thr Gln Ala Glu Gln Leu Thr Lys Cys Glu Val Phe Gln Lys Leu Lys
                20                  25                  30

Asp Leu Lys Asp Tyr Gly Gly Val Ser Leu Pro Glu Trp Val Cys Thr
                35                  40                  45

Ala Phe His Thr Ser Gly Tyr Asp Thr Gln Ala Ile Val Gln Asn Asn
        50                  55                  60

Asp Ser Thr Glu Tyr Gly Leu Phe Gln Ile Asn Asn Lys Ile Trp Cys
65                  70                  75                  80

Lys Asp Asp Gln Asn Pro His Ser Arg Asn Ile Cys Asn Ile Ser Cys
                85                  90                  95

Asp Lys Phe Leu Asp Asp Leu Thr Asp Asp Ile Val Cys Ala Lys
                100                 105                 110

Lys Ile Leu Asp Lys Val Gly Ile Asn Tyr Trp Leu Ala His Lys Ala
                115                 120                 125

Leu Cys Ser Glu Lys Leu Asp Gln Trp Leu Cys Glu Lys Leu
                130                 135                 140
```

<210> SEQ ID NO 10
<211> LENGTH: 735
<212> TYPE: DNA
<213> ORGANISM: Capra hircus

<400> SEQUENCE: 10

```
gggggggtaac caaaatgatg tcctttgtct ctctgctcct ggtaggcatc ctgttccacg    60
ccacccaggc tgaacaatta acaaaatgtg aggtgttcca gaagctgaag gacttgaagg   120
actacggagg tgtcagtttg cctgaatggg tctgtactgc atttcatacc agtggttatg   180
acacacaagc catagtacaa aacaatgaca gcacagaata tggactcttc cagataaata   240
ataaaatttg gtgcaaagac gaccagaacc ctcactcaag gaacatctgt aacatctcct   300
gtgacaagtt cctggatgat gatcttactg atgacattgt gtgtgccaag aagattctgg   360
ataaagtagg aattaactac tggttggccc ataaagcact ctgttctgag aagctggatc   420
agtggctctg tgagaagttg tgaacacctg ctgtctttgc tgcttctgtc ctctttctgt   480
tcctggaact cctctgcccc ttggctacct cgttttgctt ctttgtaccc ccttgaagct   540
aactcgtctc tgagccctgg gccctgtagt gacgatggac atgtaaggac taatctccag   600
ggatgcgtga atggtgctca ggacatttga cccttgctcg gtgccctga tagcactttt    660
aatgcaacag tgcatattcc acttctgtcc tgaataaaag gcctgattct gaaaaaaaaa   720
aaaaaaaaaa aaaaa                                                    735
```

<210> SEQ ID NO 11
<211> LENGTH: 142
<212> TYPE: PRT
<213> ORGANISM: Bubalus bubalis

<400> SEQUENCE: 11

```
Met Met Ser Phe Val Ser Leu Leu Val Gly Ser Leu Phe His Ala
1               5                   10                  15

Thr Gln Ala Glu Gln Leu Thr Lys Cys Glu Val Phe Arg Glu Leu Arg
                20                  25                  30

Asp Leu Lys Asp Tyr Gly Gly Val Ser Leu Pro Glu Trp Val Cys Thr
                35                  40                  45

Ala Phe His Thr Ser Gly Tyr Asp Thr Gln Ala Ile Val Gln Asn Asn
        50                  55                  60
```

```
Asp Ser Thr Glu Tyr Gly Leu Phe Gln Ile Asn Asn Lys Ile Trp Cys
65                  70                  75                  80

Lys Asp Asp Gln Asn Pro His Ser Ser Asn Ile Cys Asn Ile Ser Cys
                85                  90                  95

Asp Lys Phe Leu Asp Asp Asp Leu Thr Asp Asp Ile Met Cys Val Lys
            100                 105                 110

Lys Ile Leu Asp Lys Val Gly Ile Asn Tyr Trp Leu Ala His Lys Ala
            115                 120                 125

Leu Cys Ser Glu Lys Leu Asp Gln Trp Leu Cys Glu Lys Leu
            130                 135                 140

<210> SEQ ID NO 12
<211> LENGTH: 429
<212> TYPE: DNA
<213> ORGANISM: Bubalus bubalis

<400> SEQUENCE: 12
atgatgtcct ttgtctctct gctcctggta ggcagcctat tccatgccac ccaggcagaa      60
caattaacaa aatgtgaggt gttccgggag ctgagagact tgaaggacta cggaggtgtc     120
agtttgcctg aatgggtctg taccgcgttt cataccagtg gttatgacac acaagccata     180
gtacaaaaca atgacagcac agaatatgga ctcttccaga taaataataa aatttggtgc     240
aaagacgacc agaaccctca ctcaagcaac atctgtaaca tctcctgtga caagttcctg     300
gatgatgatc ttactgatga cattatgtgt gtcaagaaga ttctggataa agtaggaatt     360
aactactggt tggcccataa agcactctgt tctgagaagc tggatcagtg gctctgtgag     420
aagttgtga                                                            429
```